(12) United States Patent
Kuberasampath et al.

(10) Patent No.: US 6,194,376 B1
(45) Date of Patent: Feb. 27, 2001

(54) METHOD FOR MODULATING INFLAMMATORY RESPONSE COMPRISING ADMINISTERING MORPHOGEN

(75) Inventors: Thangavel Kuberasampath; Roy H. L. Pang; Hermann Oppermann, all of Medway; David C. Rueger, Hopkinton; Charles M. Cohen, Medway, all of MA (US)

(73) Assignee: Creative BioMolecules, Inc., Boston, MA (US)

( * ) Notice: Subject to any disclaimer, the term of this patent is extended or adjusted under 35 U.S.C. 154(b) by 0 days.

(21) Appl. No.: 08/414,033

(22) Filed: Mar. 30, 1995

Related U.S. Application Data

(63) Continuation of application No. 08/089,424, filed on Jul. 7, 1993, now abandoned, which is a continuation of application No. 07/753,059, filed on Aug. 30, 1991, now abandoned, which is a continuation-in-part of application No. 07/667,274, filed on Mar. 11, 1991, now abandoned.

(51) Int. Cl.$^7$ .................................................. A61K 38/18

(52) U.S. Cl. .................................. 514/2; 514/8; 514/12

(58) Field of Search ............................... 514/2, 8, 12

(56) References Cited

U.S. PATENT DOCUMENTS

| | | | |
|---|---|---|---|
| 4,450,159 | 5/1984 | Anderson et al. | 424/246 |
| 4,657,760 | 4/1987 | Kung et al. | 424/85 |
| 4,772,606 | 9/1988 | Sircar et al. | 514/262 |
| 4,806,523 * | 2/1989 | Bentz et al. | 514/2 |
| 4,921,858 | 5/1990 | Malone et al. | 514/258 |
| 4,952,409 | 8/1990 | Bando et al. | 424/450 |
| 4,959,302 | 9/1990 | Cornaby et al. | 435/5 |
| 4,968,590 | 11/1990 | Kuberasampath et al. | 530/326 |
| 4,968,701 | 11/1990 | Ackerman et al. | 514/312 |
| 4,971,952 * | 11/1990 | Bantz et al. | 514/12 |
| 4,975,526 | 12/1990 | Kuberasampath et al. | 530/350 |
| 5,002,965 * | 3/1991 | Ramwell et al. | 424/423 |
| 5,008,240 * | 4/1991 | Bentz et al. | 514/2 |
| 5,008,246 | 4/1991 | Schön et al. | 514/18 |
| 5,011,691 | 4/1991 | Oppermann et al. | 424/423 |
| 5,013,649 | 5/1991 | Wang et al. | 435/69.1 |
| 5,108,753 | 4/1992 | Kuberasampath et al. | 424/422 |
| 5,118,791 | 6/1992 | Burnier et al. | 514/12 |
| 5,135,915 | 8/1992 | Czarniecki et al. | 514/21 |
| 5,141,905 | 8/1992 | Rosen et al. | 435/69.1 |
| 5,221,734 * | 6/1993 | Burk et al. | 530/399 |
| 5,462,925 * | 10/1995 | Ogawa et al. | 514/12 |

FOREIGN PATENT DOCUMENTS

| | | | |
|---|---|---|---|
| 0269408 * | 6/1988 | (EP) . | |
| 8909787 | 10/1989 | (WO) | C07K/13/00 |
| 8909788 | 10/1989 | (WO) | C07K/13/00 |
| 9000900 * | 2/1990 | (WO) . | |
| 91/05802 | 5/1991 | (WO) | C07K/15/00 |
| 92/07073 | 4/1992 | (WO) | C07K/15/00 |
| 92/15323 | 9/1992 | (WO) | A61K/37/12 |

OTHER PUBLICATIONS

Hammond et al. Can. J. Physiol. Pharmacol. 63:173–187, 1985.*
Joyce et al. Annals of the New York Academy of Sciences 593:107–123, 1990.*
Puolakkainen et al. Journal of Surgical Research 58(3):321–329, Mar. 1995.*
Beck et al. Journal of Bone and Mineral Research 6(11):1257–1265, Nov. 1991.*
Noda et al. Endocrinology 124(6):2991–2994, Jun. 1989.*
Özkaynak et al, *EMBO J.*, vol. 9, 1990, pp. 2085–2093.*
Mason, (1985), Nature 318:659–663.*
Cate, et al., (1986), Cell 45:685–698.*
Forage et al., (1986), Proc. Natl. Acad. Sci. USA 83:3091–3095.*
Farah et al. (1994) 28 *Cardiovascular Research* 1226–1230.*
Entman et al. (1994) 28 *Cardiovascular Research* 1301–1311.*
Leor et al. (1994) 45 *Angiology* 8:717–724.*
Lefer et al. (1993) 33 *Annu. Rev. Pharmacol. Toxicol.* 71–90.*
Gennaro (1990) Remington's Pharmaceutical Sciences (Mack Publishers, N.Y.).*
Celeste et al., "Identification of Transforming Growth Factor Beta Family Members Present in Bone–Inductive Protein Purified From Bovine Bone", Proc. Nat. Acad. Sciences, vol. 87, pp. 9843–9847, Dec. 1990.*
George et al. (1988) Macromolecular Sequencing and Synthesis: Selected Methods & Applications (Alan R. Liss, Inc., N.Y.) pp. 127–149.*
Sampath et al. (1983), "Homology of Bone–Inductive Proteins From Human, Monkey, Bovine, and Rat Extracellular Matrix," 80 *Proc. Nat'l. Acad. Sci. USA* 6591–6595.*
Bentz et al. (1987), "Cartilage Induction and Differentiation: The Role of Bone Derived Cartilage Inducing Factor (CIF–A)," *Dev. & Diseases of Cartil. & Bone Matrix* 137–147.*

(List continued on next page.)

*Primary Examiner*—Elizabeth Kemmerer
(74) *Attorney, Agent, or Firm*—Ivor R. Elrifi; Mintz, Levin, Cohn, Ferris, Glovsky and Popeo; Michel Morency

(57) ABSTRACT

The invention provides methods for alleviating immune cell mediated inflammatory responses to injury to mammalian tissue. The present methods make use of osteogenic protein 1(OP-1), which is appreciated herein as tissue morphogen, i.e., a substance competent to induce tissue-specific morphogenesis of mammalian body tissues in addition to bone and/or cartilage. Alternatively, the present methods make use of other naturally-occurring or biosynthetic proteins sharing a defined structural and functional relationship with OP-1 and thus appreciated herein also to be tissue morphogens. The invention is particularly adapted to alleviating tissue damage associated with ischemia-reperfusion injury or hyperoxia injury in mammals, including humans.

24 Claims, 3 Drawing Sheets

OTHER PUBLICATIONS

Ruscetti et al. (1991), "Transforming Growth Factor–β And The Immune System," 3 *Prog. Growth Factor Res.* 159–175.*

Sporn et al. (1992), "Transforming Growth Factor–β: Recent Progress and New Challenges," 119 *J. Cell Biol.* 1017–1021.*

Gross et al. (1993), "Transforming Growth Factor–β1 Reduces Infarct Size After Experimental Cerebral Ischemia in a Rabbit Model," 24 *Stroke* 558–562.*

Reddi et al. (1993), "Initiation and Promotion of Bone Differentiation by Bone Morphogenetic Proteins," 8 *J. Bone Min. Res.* 2:S499–S502.*

Sampath et al. (1994), "Structure, Function, and Orthopedic Applications of Osteogenic Protein–1 (OP–1)," *Complications in Orthop.* 101–107.*

Christian et al "Synapse Formation Between Two Conal Cell Lines", *Science 196*:995–998 (May 1977).*

Ouellette et al. "Expression of Two 'Immediate Early' Genes in Response to Renal Ischemiaon", *J. Clin. Invest.* 85:766–771 (Mar. 1990).*

Phillips et al "The Effects of a New Tissue Plasminagen Activator Analog . . . " *Annals of Neurol.* 25(3): 281–285 (1989).*

Perides et al, "Neuroprotective effect of human osteogenic protein 1 . . . " *Neurosci. Lett.* (187):21–24 (1995).*

* cited by examiner–

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
       (A) LENGTH: 97 amino acids
       (B) TYPE: amino acid
       (C) STRANDEDNESS: single
       (D) TOPOLOGY: linear (ii) MOLECULE TYPE: protein (ix) FEATURE:
       (A) NAME/KEY: Protein
       (B) LOCATION: 1..97
       (D) OTHER INFORMATION: /label= GENERIC-SEQ-1
           /note= "Each Xaa indicates one of the 20 naturally-
             occurring L-isomer, alpha-amino acids, or a derivative
             thereof."

(xi) SEQUENCE DESCRIPTION: SEQ ID NO:1:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Cys Xaa Xaa Xaa Cys Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Cys Cys Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Cys Xaa Cys
            85                  90                  95

Xaa (2) INFORMATION FOR SEQ ID NO:2:

(i) SEQUENCE CHARACTERISTICS:
       (A) LENGTH: 97 amino acids
       (B) TYPE: amino acid
       (C) STRANDEDNESS: single
       (D) TOPOLOGY: linear (ii) MOLECULE TYPE: protein (ix) FEATURE:
       (A) NAME/KEY: Protein
       (B) LOCATION: 1..97
       (D) OTHER INFORMATION: /label= GENERIC-SEQ-2
           /note= "Each Xaa indicates one of the 20 naturally-
             occurring L-isomer, alpha-amino acids, or a derivative
             thereof."

(xi) SEQUENCE DESCRIPTION: SEQ ID NO:2:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Xaa Xaa Xaa Cys Xaa Xaa Xaa
            20                  25                  30

Xaa Xaa Xaa Cys Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Cys Cys Xaa Xaa

```
                   50                  55                  60
Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Cys Xaa Cys
                 85                  90                  95

Xaa
```

(2) INFORMATION FOR SEQ ID NO:3:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= GENERIC-SEQ-3
            /note= "Wherein each Xaa is independently selected from
            a group of one or more specified amino acids as defined
            in the specification."

(xi) SEQUENCE DESCRIPTION: SEQ ID NO:3:

```
Leu Tyr Val Xaa Phe Xaa Xaa Xaa Gly Trp Xaa Xaa Trp Xaa Xaa Ala
  1               5                  10                  15

Pro Xaa Gly Xaa Xaa Ala Xaa Tyr Cys Xaa Gly Xaa Cys Xaa Xaa Pro
                 20                  25                  30

Xaa Xaa Xaa Xaa Xaa Xaa Xaa Xaa Asn His Ala Xaa Xaa Xaa Xaa Leu
             35                  40                  45

Xaa Xaa Xaa Xaa Xaa Xaa Xaa Xaa Xaa Xaa Xaa Xaa Cys Cys Xaa Pro
         50                  55                  60

Xaa Xaa Xaa Xaa Xaa Xaa Xaa Leu Xaa Xaa Xaa Xaa Xaa Xaa Xaa Xaa
 65                  70                  75                  80

Val Xaa Leu Xaa Xaa Xaa Xaa Xaa Met Xaa Val Xaa Xaa Cys Gly Cys
                 85                  90                  95

Xaa
```

(2) INFORMATION FOR SEQ ID NO:4:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= GENERIC-SEQ-4
            /note= "Wherein each Xaa is independently selected from
            a group of one or more specified amino acids as defined
            in the specification."

(xi) SEQUENCE DESCRIPTION: SEQ ID NO:4:

```
Cys Xaa Xaa Xaa Xaa Leu Tyr Val Xaa Phe Xaa Xaa Xaa Gly Trp Xaa
  1               5                  10                  15

Xaa Trp Xaa Xaa Ala Pro Xaa Gly Xaa Xaa Ala Xaa Tyr Cys Xaa Gly
                 20                  25                  30

Xaa Cys Xaa Xaa Pro Xaa Xaa Xaa Xaa Xaa Xaa Xaa Xaa Asn His Ala
```

```
                    35                  40                  45
    Xaa Xaa Xaa Xaa Leu Xaa Xaa Xaa Xaa Xaa Xaa Xaa Xaa Xaa Xaa
             50                  55                  60

Xaa Cys Cys Xaa Pro Xaa Xaa Xaa Xaa Xaa Xaa Xaa Leu Xaa Xaa
     65                  70                  75                  80

Xaa Xaa Xaa Xaa Xaa Val Xaa Leu Xaa Xaa Xaa Xaa Met Xaa Val
                         85                  90                  95

Xaa Xaa Cys Gly Cys Xaa
               100
```

(2) INFORMATION FOR SEQ ID NO:5:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..139
        (D) OTHER INFORMATION: /note= "hOP-1 (mature form)"

(xi) SEQUENCE DESCRIPTION: SEQ ID NO:5:

```
Ser Thr Gly Ser Lys Gln Arg Ser Gln Asn Arg Ser Lys Thr Pro Lys
 1               5                  10                  15

Asn Gln Glu Ala Leu Arg Met Ala Asn Val Ala Glu Asn Ser Ser Ser
                 20                  25                  30

Asp Gln Arg Gln Ala Cys Lys Lys His Glu Leu Tyr Val Ser Phe Arg
                 35                  40                  45

Asp Leu Gly Trp Gln Asp Trp Ile Ile Ala Pro Glu Gly Tyr Ala Ala
             50                  55                  60

Tyr Tyr Cys Glu Gly Glu Cys Ala Phe Pro Leu Asn Ser Tyr Met Asn
 65                  70                  75                  80

Ala Thr Asn His Ala Ile Val Gln Thr Leu Val His Phe Ile Asn Pro
                 85                  90                  95

Glu Thr Val Pro Lys Pro Cys Cys Ala Pro Thr Gln Leu Asn Ala Ile
                100                 105                 110

Ser Val Leu Tyr Phe Asp Asp Ser Ser Asn Val Ile Leu Lys Lys Tyr
                115                 120                 125

Arg Asn Met Val Val Arg Ala Cys Gly Cys His
             130                 135
```

(2) INFORMATION FOR SEQ ID NO:6:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..139
        (D) OTHER INFORMATION: /note= "mOP-1 (mature form)"

(xi) SEQUENCE DESCRIPTION: SEQ ID NO:6:

```
Ser Thr Gly Gly Lys Gln Arg Ser Gln Asn Arg Ser Lys Thr Pro Lys
 1               5                  10                  15
```

```
Asn Gln Glu Ala Leu Arg Met Ala Ser Val Ala Glu Asn Ser Ser Ser
                20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
            85                  90                  95

Asp Thr Val Pro Lys Pro Cys Cys Ala Pro Thr Gln Leu Asn Ala Ile
                100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
        130                 135
```

(2) INFORMATION FOR SEQ ID NO:7:

(i) SEQUENCE CHARACTERISTICS:
      (A) LENGTH: 139 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Protein
      (B) LOCATION: 1..139
      (D) OTHER INFORMATION: /note= "hOP-2 (mature form)"

(xi) SEQUENCE DESCRIPTION: SEQ ID NO:7:

```
Ala Val Arg Pro Leu Arg Arg Arg Gln Pro Lys Lys Ser Asn Glu Leu
1               5                   10                  15

Pro Gln Ala Asn Arg Leu Pro Gly Ile Phe Asp Asp Val His Gly Ser
                20                  25                  30

His Gly Arg Gln Val Cys Arg Arg His Glu Leu Tyr Val Ser Phe Gln
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ser Phe Pro Leu Asp Ser Cys Met Asn
65                  70                  75                  80

Ala Thr Asn His Ala Ile Leu Gln Ser Leu Val His Leu Met Lys Pro
            85                  90                  95

Asn Ala Val Pro Lys Ala Cys Cys Ala Pro Thr Lys Leu Ser Ala Thr
                100                 105                 110

Ser Val Leu Tyr Tyr Asp Ser Ser Asn Asn Val Ile Leu Arg Lys Ala
        115                 120                 125

Arg Asn Met Val Val Lys Ala Cys Gly Cys His
        130                 135
```

(2) INFORMATION FOR SEQ ID NO:8:

(i) SEQUENCE CHARACTERISTICS:
      (A) LENGTH: 139 amino acids
      (B) TYPE: amino acid
      (C) STRANDEDNESS: single
      (D) TOPOLOGY: linear (ii) MOLECULE TYPE: protein (ix) FEATURE:
             (A) NAME/KEY: Protein
             (B) LOCATION: 1..139
             (D) OTHER INFORMATION: /note= "mOP-2 (mature form)"

(xi) SEQUENCE DESCRIPTION: SEQ ID NO:8:

Ala Ala Arg Pro Leu Lys Arg Arg Gln Pro Lys Lys Thr Asn Glu Leu
    1               5                  10                  15

Pro His Pro Asn Lys Leu Pro Gly Ile Phe Asp Asp Gly His Gly Ser
                20                  25                  30

Arg Gly Arg Glu Val Cys Arg Arg His Glu Leu Tyr Val Arg Phe Arg
            35                  40                  45

Asp Leu Gly Trp Leu Asp Trp Val Ile Ala Pro Gln Gly Tyr Ser Ala
        50                  55                  60

Tyr Tyr Cys Glu Gly Glu Cys Ala Phe Pro Leu Asp Ser Cys Met Asn
    65                  70                  75                  80

Ala Thr Asn His Ala Ile Leu Gln Ser Leu Val His Leu Met Lys Pro
                    85                  90                  95

Asp Val Val Pro Lys Ala Cys Cys Ala Pro Thr Lys Leu Ser Ala Thr
                100                 105                 110

Ser Val Leu Tyr Tyr Asp Ser Ser Asn Val Ile Leu Arg Lys His
                115                 120                 125

Arg Asn Met Val Val Lys Ala Cys Gly Cys His
            130                 135

(2) INFORMATION FOR SEQ ID NO:9:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (ix) FEATURE:
         (A) NAME/KEY: Protein
         (B) LOCATION: 1..101
         (D) OTHER INFORMATION: /note= "CBMP-2A (fx)"

(xi) SEQUENCE DESCRIPTION: SEQ ID NO:9:

Cys Lys Arg His Pro Leu Tyr Val Asp Phe Ser Asp Val Gly Trp Asn
    1               5                  10                  15

Asp Trp Ile Val Ala Pro Pro Gly Tyr His Ala Phe Tyr Cys His Gly
                20                  25                  30

Glu Cys Pro Phe Pro Leu Ala Asp His Leu Asn Ser Thr Asn His Ala
            35                  40                  45

Ile Val Gln Thr Leu Val Asn Ser Val Asn Ser Lys Ile Pro Lys Ala
        50                  55                  60

Cys Cys Val Pro Thr Glu Leu Ser Ala Ile Ser Met Leu Tyr Leu Asp
    65                  70                  75                  80

Glu Asn Glu Lys Val Val Leu Lys Asn Tyr Gln Asp Met Val Val Glu
                    85                  90                  95

Gly Cys Gly Cys Arg
                100

(2) INFORMATION FOR SEQ ID NO:10:

(i) SEQUENCE CHARACTERISTICS:

(A) LENGTH: 101 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..101
        (D) OTHER INFORMATION: /note= "CBMP-2B (fx)"

(xi) SEQUENCE DESCRIPTION: SEQ ID NO:10:

Cys Arg Arg His Ser Leu Tyr Val Asp Phe Ser Asp Val Gly Trp Asn
    1               5                   10                  15

Asp Trp Ile Val Ala Pro Pro Gly Tyr Gln Ala Phe Tyr Cys His Gly
                    20                  25                  30

Asp Cys Pro Phe Pro Leu Ala Asp His Leu Asn Ser Thr (B) TYPE: amino acid
            (C) STRANDEDNESS: single
            (D) TOPOLOGY: linear (ii) MOLECULE TYPE: protein (ix) FEATURE:
            (A) NAME/KEY: Protein
            (B) LOCATION: 1..102
            (D) OTHER INFORMATION: /note= "Vgl (fx)"

(xi) SEQUENCE DESCRIPTION: SEQ ID NO:12:

Cys Lys Lys Arg His Leu Tyr Val Glu Phe Lys Asp Val Gly Trp Gln
    1               5                   10                  15

Asn Trp Val Ile Ala Pro Gln Gly Tyr Met Ala Asn Tyr Cys Tyr Gly
                    20                  25                  30

Glu Cys Pro Tyr Pro Leu Thr Glu Ile Leu Asn Gly Ser Asn His Ala
                35                  40                  45

Ile Leu Gln Thr Leu Val His Ser Ile Glu Pro Glu Asp Ile Pro Leu
    50                  55                  60

Pro Cys Cys Val Pro Thr Lys Met Ser Pro Ile Ser Met Leu Phe Tyr
    65                  70                  75                  80

Asp Asn Asn Asp Asn Val Val Leu Arg His Tyr Glu Asn Met Ala Val
                    85                  90                  95

Asp Glu Cys Gly Cys Arg
                    100

(2) INFORMATION FOR SEQ ID NO:13:

(i) SEQUENCE CHARACTERISTICS:
            (A) LENGTH: 102 amino acids
            (B) TYPE: amino acid
            (C) STRANDEDNESS: single
            (D) TOPOLOGY: linear (ii) MOLECULE TYPE: protein (ix) FEATURE:
            (A) NAME/KEY: Protein
            (B) LOCATION: 1..102
            (D) OTHER INFORMATION: /note= "Vgr-1 (fx)"

(xi) SEQUENCE DESCRIPTION: SEQ ID NO:13:

Cys Lys Lys His Gly Leu Tyr Val Ser Phe Gln Asp Val Gly Trp Gln
    1               5                   10                  15

Asp Trp Ile Ile Ala Pro Lys Gly Tyr Ala Ala Asn Tyr Cys Asp Gly
                    20                  25                  30

Glu Cys Ser Phe Pro Leu Asn Ala His Met Asn Ala Thr Asn His Ala
                35                  40                  45

Ile Val Gln Thr Leu Val His Val Met Asn Pro Glu Tyr Val Pro Lys
    50                  55                  60

Pro Cys Cys Ala Pro Thr Lys Val Asn Ala Ile Ser Val Leu Tyr Phe
    65                  70                  75                  80

Asp Asp Asn Ser Asn Val Ile Leu Lys Lys Tyr Arg Asn Met Val Val
                    85                  90                  95

Arg Ala Cys Gly Cys His
                    100

(2) INFORMATION FOR SEQ ID NO:14:

(i) SEQUENCE CHARACTERISTICS:
            (A) LENGTH: 106 amino acids
            (B) TYPE: amino acid (C) STRANDEDNESS: single
        (D) TOPOLOGY: linear (ii) MOLECULE TYPE: protein (ix) FEATURE:
        (A) NAME/KEY: Protein
        (B) LOCATION: 1..106
        (D) OTHER INFORMATION: /note= "GDF-1 (fx)"

(xi) SEQUENCE DESCRIPTION: SEQ ID NO:14:

Cys Arg Ala Arg Arg Leu Tyr Val Ser Phe Arg Glu Val Gly Trp His
 1               5                  10                  15

Arg Trp Val Ile Ala Pro Arg Gly Phe Leu Ala Asn Tyr Cys Gln Gly
                20                  25                  30

Gln Cys Ala Leu Pro Val Ala Leu Ser Gly Ser Gly Gly Pro Pro Ala
            35                  40                  45

Leu Asn His Ala Val Leu Arg Ala Leu Met His Ala Ala Ala Pro Gly
50                  55                  60

Ala Ala Asp Leu Pro Cys Cys Val Pro Ala Arg Leu Ser Pro Ile Ser
65                  70                  75                  80

Val Leu Phe Phe Asp Asn Ser Asp Asn Val Val Leu Arg Gln Tyr Glu
                85                  90                  95

Asp Met Val Val Asp Glu Cys Gly Cys Arg
            100                 105

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Cys Xaa Xaa Xaa Xaa
 1               5

(2) INFORMATION FOR SEQ ID NO:16:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..98
        (D) OTHER INFORMATION: /note= "COP-1"

(xi) SEQUENCE DESCRIPTION: SEQ ID NO:16:

Leu Tyr Val Asp Phe Gln Arg Asp Val Gly Trp Asp Asp Trp Ile Ile
 1               5                  10                  15

Ala Pro Val Asp Phe Asp Ala Tyr Tyr Cys Ser Gly Ala Cys Gln Phe
                20                  25                  30

Pro Ser Ala Asp His Phe Asn Ser Thr Asn His Ala Val Val Gln Thr
            35                  40                  45

Leu Val Asn Asn Met Asn Pro Gly Lys Val Pro Lys Pro Cys Cys Val
50                  55                  60

```
Pro Thr Glu Leu Ser Ala Ile Ser Met Leu Tyr Leu Asp Glu Asn Ser
65                  70                  75                  80

Thr Val Val Leu Lys Asn Tyr Gln Glu Met Thr Val Val Gly Cys Gly
                85                  90                  95

Cys Arg
```

(2) INFORMATION FOR SEQ ID NO:17:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..98
        (D) OTHER INFORMATION: /note= "COP-3"

(xi) SEQUENCE DESCRIPTION: SEQ ID NO:17:

```
Leu Tyr Val Asp Phe Gln Arg Asp Val Gly Trp Asp Asp Trp Ile Val
1               5                   10                  15

Ala Pro Pro Gly Tyr Gln Ala Phe Tyr Cys Ser Gly Ala Cys Gln Phe
                20                  25                  30

Pro Ser Ala Asp His Phe Asn Ser Thr Asn His Ala Val Val Gln Thr
                35                  40                  45

Leu Val Asn Asn Met Asn Pro Gly Lys Val Pro Lys Pro Cys Cys Val
        50                  55                  60

Pro Thr Glu Leu Ser Ala Ile Ser Met Leu Tyr Leu Asp Glu Asn Glu
65                  70                  75                  80

Lys Val Val Leu Lys Asn Tyr Gln Glu Met Val Val Glu Gly Cys Gly
                85                  90                  95

Cys Arg
```

(2) INFORMATION FOR SEQ ID NO:18:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /note= "COP-4"

(xi) SEQUENCE DESCRIPTION: SEQ ID NO:18:

```
Leu Tyr Val Asp Phe Ser Asp Val Gly Trp Asp Trp Ile Val Ala
1               5                   10                  15

Pro Pro Gly Tyr Gln Ala Phe Tyr Cys Ser Gly Ala Cys Gln Phe Pro
                20                  25                  30

Ser Ala Asp His Phe Asn Ser Thr Asn His Ala Val Val Gln Thr Leu
                35                  40                  45

Val Asn Asn Met Asn Pro Gly Lys Val Pro Lys Pro Cys Cys Val Pro
        50                  55                  60

Thr Glu Leu Ser Ala Ile Ser Met Leu Tyr Leu Asp Glu Asn Glu Lys
65                  70                  75                  80
```

Val Val Leu Lys Asn Tyr Gln Glu Met Val Val Glu Gly Cys Gly Cys
             85                  90                  95

Arg (2) INFORMATION FOR SEQ ID NO:19:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: protein (ix) FEATURE:
         (A) NAME/KEY: Protein
         (B) LOCATION: 1..96
         (D) OTHER INFORMATION: /note= "COP-5"

(xi) SEQUENCE DESCRIPTION: SEQ ID NO:19:

Leu Tyr Val Asp Phe Ser Asp Val Gly Trp Asp Asp Trp Ile Val Ala
1               5                   10                  15

Pro Pro Gly Tyr Gln Ala Phe Tyr Cys His Gly Glu Cys Pro Phe Pro
             20                  25                  30

Leu Ala Asp His Phe Asn Ser Thr Asn His Ala Val Val Gln Thr Leu
             35                  40                  45

Val Asn Ser Val Asn Ser Lys Ile Pro Lys Ala Cys Cys Val Pro Thr
    50                  55                  60

Glu Leu Ser Ala Ile Ser Met Leu Tyr Leu Asp Glu Asn Glu Lys Val
65                  70                  75                  80

Val Leu Lys Asn Tyr Gln Glu Met Val Val Glu Gly Cys Gly Cys Arg
             85                  90                  95

(2) INFORMATION FOR SEQ ID NO:20:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: protein (ix) FEATURE:
         (A) NAME/KEY: Protein
         (B) LOCATION: 1..96
         (D) OTHER INFORMATION: /note= "COP-7"

(xi) SEQUENCE DESCRIPTION: SEQ ID NO:20:

Leu Tyr Val Asp Phe Ser Asp Val Gly Trp Asn Asp Trp Ile Val Ala
1               5                   10                  15

Pro Pro Gly Tyr His Ala Phe Tyr Cys His Gly Glu Cys Pro Phe Pro
             20                  25                  30

Leu Ala Asp His Leu Asn Ser Thr Asn His Ala Val Val Gln Thr Leu
             35                  40                  45

Val Asn Ser Val Asn Ser Lys Ile Pro Lys Ala Cys Cys Val Pro Thr
    50                  55                  60

Glu Leu Ser Ala Ile Ser Met Leu Tyr Leu Asp Glu Asn Glu Lys Val
65                  70                  75                  80

Val Leu Lys Asn Tyr Gln Glu Met Val Val Glu Gly Cys Gly Cys Arg
             85                  90                  95

(2) INFORMATION FOR SEQ ID NO:21:

```
    (i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..96
        (D) OTHER INFORMATION: /note= "COP-16"

(xi) SEQUENCE DESCRIPTION: SEQ ID NO:21:

Leu Tyr Val Asp Phe Ser Asp Val Gly Trp Asn Asp Trp Ile Val Ala
   1               5                   10                  15

Pro Pro Gly Tyr Gln Ala Phe Tyr Cys His Gly Glu Cys Pro Phe Pro
                   20                  25                  30

Leu Ala Asp His Phe Asn Ser Thr Asn His Ala Val Val Gln Thr Leu
                   35                  40                  45

Val Asn Ser Val Asn Ser Lys Ile Pro Lys Ala Cys Cys Val Pro Thr
           50                  55                  60

Glu Leu Ser Ala Ile Ser Met Leu Tyr Leu Asp Glu Asn Glu Lys Val
   65                  70                  75                  80

Val Leu Lys Asn Tyr Gln Glu Met Val Val Glu Gly Cys Gly Cys Arg
                       85                  90                  95
```

METHOD FOR MODULATING INFLAMMATORY RESPONSE COMPRISING ADMINISTERING MORPHOGEN

RELATIONSHIP TO RELATED APPLICATIONS

This is a continuation of U.S. Ser. No. 08/089,424, filed on Jul. 7, 1993, now abandoned, as a continuation of now-abandoned U.S. Ser. No. 07/753,059, filed on Aug. 30, 1991 as a continuation-in-part of now-abandoned U.S. Ser. No. 07/667,274, filed Mar. 11, 1991. Incorporated herein by reference are the contents of copending U.S. Ser. No. 08/404,113, filed Mar. 14, 1995, as a continuation of now-abandoned U.S. Ser. No. 08/091,395, filed Jul. 13, 1993 as a continuation of now-abandoned U.S. Ser. No. 07/752,764, filed Aug. 30, 1991 as a continuation-in-part of now-abandoned U.S. Ser. No. 07/667,274, filed Mar. 11, 1991.

FIELD OF THE INVENTION

The present invention relates generally to a method for modulating the inflammatory response induced in a mammal following tissue injury. More particularly, this invention relates to a method for alleviating the tissue destructive effects associated with the inflammatory response. In a particular embodiment of the invention, this invention provides a method for alleviating immune cell-mediated tissue destruction following the initial tissue injury associated with oxygen deprivation to a tissue, such as can occur from ischemic-reperfusion injury, or following the initial tisue injury associated with high oxygen concentrations (hyperoxia).

BACKGROUND OF THE INVENTION

The body's inflammatory response to tissue injury can cause significant tissue destruction, leading to loss of tissue function. Damage to cells resulting from the effects of inflammatory response has been implicated as the cause of reduced tissue function or loss of tissue function in diseases of the joints (e.g., rheumatoid and osteo-arthritis) and of many organs, including the kidney, pancreas, skin, lung and heart. For example, glomerular nephritis, diabetes, inflammatory bowel disease, vascular diseases such as atherocleresis and vasculitis and skin diseases such as psoriasis and dermatitis are believed to result in large part from unwanted acute inflammatory reaction. Graft rejection also is believed to be primarily due to the action of the body's immune/inflammatory response system.

A variety of lung diseases also are characterized by airway inflammation, including chronic bronchitis, emphysema, idiopathic pulmonary fibrosis and asthma. Another dysfunction associated with the inflammatory response is that mounted in response to injury caused by hyperoxia, e.g., prolonged exposure to lethally high concentrations of $O_2$ (95–100% $O_2$). Similarly, reduced blood flow to a tissue (and, therefore reduced or lack of oxygen to tissues), as described below, also can induce a primary tissue injury that stimulates the inflammatory response.

It is well known that damage occurs to cells in mammals which have been deprived of oxygen. In fact, the interruption of blood flow, whether partial (hypoxia) or complete (ischemia) and the ensuing inflammatory responses may be the most important cause of coagulative necrosis or cell death in human disease. The complications of atherosclerosis, for example, are generally the result of ischemic cell injury in the brain, heart, small intestines, kidneys, and lower extremities. Highly differentiated cells, such as the proximal tubular cells of the kidney, cardiac myocytes, and the neurons of the central nervous system, all depend on aerobic respiration to produce ATP, the energy necessary to carry out their specialized functions. When ischemia limits the oxygen supply and ATP is depleted, the affected cells may become irreversibly injured. The ensuing inflammatory responses to this initial injury provide additional insult to the affected tissue. Examples of such hypoxia or ischemia are the partial or total loss of blood supply to the body as a whole, an organ within the body, or a region within an organ, such as occurs in cardiac arrest, pulmonary embolus, renal artery occlusion, coronary occlusion or occlusive stroke.

The tissue damage associated with ischemia-reperfusion injury is believed to comprise both the initial cell damage induce by the deprivation of oxygen to the cell and its subsequent recirculation, as well as the damage caused by the body's response to this initial damage. The secondary damage, resulting from the inflammatory response, is likely the source of significant tissue damage. It is thought that reperfusion may result in dysfunction to the endothelium of the vasculature as well as injury to the surrounding tissue. Among the factors thought to mediate these damaging effects are those associated with modulating the body's inflammatory response following tissue injury, e.g., cytokines such as interleukin-1 (IL-1) and tumor necrosis factor (TNF), and oxygen-derived free radicals such as superoxide anions. These humoral agents are produced by adhering neutrophilic leukocytes or by endothelial cells and have been identified at ischemic sites upon reperfusion. Moreover, TNF concentrations are increased in humans after myocardial infarction. The tissue damage associated with hyperoxia injury is believed to follow a similar mechanism, where the initial damage is mediated primarily through the presence of toxic oxygen metabolites.

As embodied herein, the term "ischemic-reperfusion injury" refers to the initial damage associated with oxygen deprivation of a cell and the subsequent damage associated with the inflammatory response when the cell is resupplied with oxygen. As embodied herein, the term "hyperoxia" refers to the initial tissue damage associated with prolonged exposure to lethally high doses of oxygen, e.g., greater than 95% $O_2$) and to the subsequent damage associated with the inflammatory response. Accordingly, as used herein, "toxic oxygen concentrations" refers to both lethally low oxygen concentrations or lack of oxygen, and to lethally high oxygen concentrations. Further, the expression "alleviating" means the protection from, reduction of and/or elimination of such injury.

Therefore, an object of the present invention is to provide a method for protecting mammalian tissue, particularly human tissue, from the damage associated with the inflammatory response following a tissue injury. Another object of the invention is to provide a method for alleviating tissue damage associated with ischemic-reperfusion injury in a mammal following a deprivation of, oxygen to a tissue in the mammal. A further object is to provide a method for alleviating tissue damaged associated with hyperoxia-induced tissue injury. Still another object of the invention is to provide a method for modulating the inflammatory responses in general, particularly those induced in a human following tissue injury.

Other objects of the present invention include providing a method for alleviating tissue damage associated with ischemic-reperfusion injury in a human which has suffered from hypoxia or ischemia following cardiac arrest, pulmonary embolus, renal artery occlusion, coronary occlusion or occlusive stroke, as well as a method for alleviating tissue damage associated with hyperoxia in a human following exposure to lethally high oxygen concentrations.

These and other objects and features of the invention will be apparent from the description, drawings and claims which follow.

SUMMARY OF THE INVENTION

The present invention provides a method for alleviating the tissue destructive effects associated with activation of the inflammatory response following tissue injury. The method comprises the step of administering to the animal a therapeutically effective amount of a morphogenic protein ("morphogen", as defined herein) upon tissue injury, for a time and at a concentration sufficient to significantly inhibit or reduce the tissue destructive effects of the inflammatory response. In one preferred embodiment of the invention, the invention provides a method for alleviating the ischemic-reperfusion injury in mammalian tissue resulting from a deprivation of, and subsequent reperfusion of oxygen to the tissue. In another preferred embodiment, the invention provides a method for alleviating the tissue-destructive effects associated with hyperoxia.

The morphogens useful in the method of this invention are members of a family of proteins sharing a conserved six or seven cysteine skeleton in their C-terminal regions, as well as other conserved amino acids, and which are capable of inducing, in addition to bone and bone cartilage, tissue-specific morphogenesis for a variety of other organs and tissues. The proteins apparently bind to surface receptors or otherwise contact and interact with progenitor cells, predisposing or stimulating the cells to proliferate and differentiate in a morphogenically permissive environment. Thus, the morphogens are capable of stimulating the proliferation and tissue-specific differentiation of progenitor cells, as well as supporting the growth and maintenance of differentiated cells, including their redifferentiation. Further details of this protein family are disclosed in copending U.S. Ser. No. 08/404,113, filed Mar. 14, 1995, pending, as a continuation of now-abandoned U.S. Ser. No. 08/091,395, filed Jul. 13, 1993 as a continuation of now-abandoned U.S. Ser. No. 07/752,764, filed Aug. 30, 1991 as a continuation-in-part of now-abandoned U.S. Ser. No. 07/667,274, filed Mar. 11, 1991, the disclosures of which are hereby incorporated by reference.

Among the members of this protein family identified to date, all of which are members of the TGF-β super family of proteins, are OP1, OP2, CBMP2, DPP, Vgl, Vgr-1, and GDF-1. Table I, below, describes the various morphogens identified to date, including their nomenclature as used herein, and Seq. ID references. The terms "OP1" and "OP2" also are referred to in related applications as "OP-1" and "OP-2".

TABLE I

| "OP1" | refers generically to the group of active proteins expressed from part or all of a DNA sequence encoding OP1 protein, e.g., human OP1 ("hOP1", Seq. ID No. 5, mature protein amino acid sequence), or mouse OP1 ("mOP1", Seq. ID No. 6, mature protein amino acid sequence.) The conserved seven cysteine skeleton is defined by residues 38 to 139 of Seq. ID Nos. 5 and 6 |

TABLE I-continued

| "OP2" | refers generically to the group of active proteins expressed from part or all of a DNA sequence encoding OP2 protein, e.g., human OP2 ("hOP2", Seq. ID No. 7, mature protein amino acid sequence) or mouse OP2 ("mOP2", Seq. ID No. 8, mature protein amino acid sequence). The conserved seven cysteine skeleton is defined by residues 38 to 139 of Seq. ID Nos. 7 and 8 |
| "CBMP2" | refers generically to the active proteins expressed from a DNA sequence encoding CBMP2A DNA protein, e.g., human CBMP2 ("CBMP2A(fx)", Seq ID No. 9) or bovine CBMP2B DNA ("CBMP2B(fx)", Seq. ID No. 10). |
| "Vgl(fx)" | refers to protein sequences encoded by the xenopus Vgl gene and defining the conserved seven cysteine skeleton (Seq. ID No. 12). |
| "Vgr-1(fx)" | refers to protein sequences encoded by the murine Vgr-1 gene and defining the conserved seven cysteine skeleton (Seq. ID No. 13). |
| "DPP(fx)" | refers to protein sequences encoded by the Drosophila DPP gene and defining the conserved seven cysteine skeleton (seq. ID No. 11). |
| "GDF-1(fx)" | refers to protein sequences encoded by the human GDF-1 gene and defining the conserved seven cysteine skeleton (seq. ID No. 14). |

The OP2 proteins have an extra cysteine residue in their C-terminal region in addition to the conserved seven cysteine skeleton they share with the other morphogens. The GDF-1 protein has a four amino acid insert within the conserved skeleton, (residues 44 to 47 of Seq. ID No. 14), but this insert likely does not interfere with the relationship of the cysteines in the folded structure. Similarly, the CBMP2 proteins have a one amino acid deletion within the skeleton (See Table II).

The morphogens are inactive when reduced, but are active as oxidized homodimers and as various oxidized heterodimers. Thus, as defined herein, a morphogen of this invention is a dimeric protein comprising a pair of polypeptide chains, wherein each polypeptide chain comprises at least the C-terminal six cysteine skeleton defined by residues 43–139 of Seq. ID No. 5, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. Specifically, the protein is capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of these cells. In addition, it is also anticipated that the morphogens of this invention will be capable of inducing dedifferentiation of committed cells under appropriate environmental conditions. Accordingly, as will be appreciated by those skilled in the art, the morphogens of this invention may be used to repair the damaged tissue, as disclosed in copending U.S. Ser. No. 08/404,113, filed Mar. 14, 1995, pending, as a continuation of now-abandoned U.S. Ser. No. 08/091,395, filed Jul. 13, 1993 as a continuation of now-abandoned U.S. Ser. No. 07/752,764, filed Aug. 30, 1991 as a continuation-in-part of now-abandoned U.S. Ser. No. 07/667,274, filed March 11, 1991, and the disclosures of which are incorporated herein by reference.

In one preferred aspect, the morphogens of this invention comprise one of two species of generic amino acid sequences: Generic Sequence 1 (Seq. ID No. 1) or Generic Sequence 2 (Seq. ID No. 2); where each Xaa indicates one of the 20 naturally-occurring L-isomer, α-amino acids or a derivative thereof. Generic Sequence 1 comprises the conserved six cysteine skeleton and Generic Sequence 2 comprises the conserved six cysteine skeleton plus the additional cysteine identified in OP2. In another preferred aspect, these sequences further comprise the following sequence at their N-terminus: (SEQ. ID NO.15)

Cys$_1$Xaa Xaa Xaa Xaa$_5$

Preferred amino acid sequences within the foregoing generic sequences include: Generic Sequence 3 (Seq. ID No. 3) and Generic Sequence 4 (Seq. ID No. 4) which accommodate the homologies shared among the members of this morphogen family identified to date (see below.) Note that these generic sequences allow for an additional cysteine at position 41 or 46 in Generic Sequences 3 or 4, respectively, providing an appropriate cysteine skeleton where inter- or intramolecular disulfide bonds can form, and contain certain critical amino acids which influence the tertiary structure of the proteins.

Generic Sequence 3

```
    Leu Tyr Val Xaa Phe
    1               5
Xaa Xaa Xaa Gly Trp Xaa Xaa Trp Xaa
                10
Xaa Ala Pro Xaa Gly Xaa Xaa Ala
15                      20
Xaa Tyr Cys Xaa Gly Xaa Cys Xaa
    25                      30
Xaa Pro Xaa Xaa Xaa Xaa Xaa
                35
Xaa Xaa Xaa Asn His Ala Xaa Xaa
        40                  45
Xaa Xaa Leu Xaa Xaa Xaa Xaa Xaa
                50
Xaa Xaa Xaa Xaa Xaa Xaa Xaa Cys
    55                      60
Cys Xaa Pro Xaa Xaa Xaa Xaa Xaa
            65
Xaa Xaa Xaa Leu Xaa Xaa Xaa
70                      75
Xaa Xaa Xaa Xaa Val Xaa Leu Xaa
            80
Xaa Xaa Xaa Xaa Met Xaa Val Xaa
85                      90
Xaa Cys Gly Cys Xaa
            95
``` wherein each Xaa is independently selected from a group of one or more specified amino acids defined as follows: "Res." means "residue" and Xaa at res.4=(Ser, Arg, Asp or Glu); Xaa at res.6=(Arg, Gln, Ser or Lys); Xaa at res.7=(Asp or Glu); Xaa at res.8=(Leu or Val); Xaa at res.11=(Gln, Leu, Asp, His or Asn); Xaa at res.12=(Asp, Arg or Asn); Xaa at res.14=(Ile or Val); Xaa at res.15=(Ile or Val); Xaa at res.18=(Glu, Gln, Leu, Lys, Pro or Arg); Xaa at res.20=(Tyr or Phe); Xaa at res.21=(Ala, Ser, Asp, Met, His, Leu or Gln); Xaa at res.23=(Tyr, Asn or Phe); Xaa at res.26=(Glu, His, Tyr, Asp or Gln); Xaa at res.28=(Glu, Lys, Asp or Gln); Xaa at res.30=(Ala, Ser, Pro or Gln); Xaa at res.31=(Phe, Leu or Tyr); Xaa at res.33=(Leu or Val); Xaa at res.34=(Asn, Asp, Ala or Thr); Xaa at res.35=(Ser, Asp, Glu, Leu or Ala); Xaa at res.36=(Tyr, Cys, His, Ser or Ile); Xaa at res.37=(Met, Phe, Gly or Leu); Xaa at res.38=(Asn or Ser); Xaa at res.39=(Ala, Ser or Gly); Xaa at res.40=(Thr, Leu or Ser); Xaa at res.44=(Ile or Val); Xaa at res.45=(Val or Leu); Xaa at res.46=(Gln or Arg); Xaa at res.47=(Thr, Ala or Ser); Xaa at res.49=(Val or Met); Xaa at res.50=(His or Asn); Xaa at res.51=(Phe, Leu, Asn, Ser, Ala or Val); Xaa at res.52=(Ile, Met, Asn, Ala or Val); Xaa at res.53=(Asn, Lys, Ala or Glu); Xaa at res.54=(Pro or Ser); Xaa at res.55=(Glu, Asp, Asn, or Gly); Xaa at res.56=(Thr, Ala, Val, Lys, Asp, Tyr, Ser or Ala); Xaa at res.57=(Val, Ala or Ile); Xaa at res.58=(Pro or Asp); Xaa at res.59=(Lys or Leu); Xaa at res.60=(Pro or Ala); Xaa at res.63=(Ala or Val); Xaa at res.65=(Thr or Ala); Xaa at res.66=(Gln, Lys, Arg or Glu); Xaa at res.67=(Leu, Met or Val); Xaa at res.68=(Asn, Ser or Asp); Xaa at res.69=(Ala, Pro or Ser); Xaa at res.70=(Ile, Thr or Val); Xaa at res.71=(Ser or Ala); Xaa at res.72=(Val or Met); Xaa at res.74=(Tyr or Phe); Xaa at res.75=(Phe, Tyr or Leu); Xaa at res.76=(Asp or Asn); Xaa at res.77=(Asp, Glu, Asn or Ser); Xaa at res.78=(Ser, Gln, Asn or Tyr); Xaa at res.79=(Ser, Asn, Asp or Glu); Xaa at res.80=(Asn, Thr or Lys); Xaa at res.82=(Ile or Val); Xaa at res.84=(Lys or Arg); Xaa at res.85=(Lys, Asn, Gln or His); Xaa at res.86=(Tyr, Ala or His); Xaa at res.87=(Arg, Gln or Glu); Xaa at res.88=(Asn, Glu or Asp); Xaa at res.90=(Val, Thr or Ala); Xaa at res.92=(Arg, Lys, Val, Asp or Glu); Xaa at res.93=(Ala, Gly or Glu); and Xaa at res.97=(His or Arg).

Generic Sequence 4

```
Cys Xaa Xaa Xaa Xaa Leu Tyr Val Xaa Phe
1               5                   10
Xaa Xaa Xaa Gly Trp Xaa Xaa Trp Xaa
                15
Xaa Ala Pro Xaa Gly Xaa Xaa Ala
20                      25
Xaa Tyr Cys Xaa Gly Xaa Cys Xaa
        30                      35
Xaa Pro Xaa Xaa Xaa Xaa Xaa
                40
Xaa Xaa Xaa Asn His Ala Xaa Xaa
            45                  50
Xaa Xaa Leu Xaa Xaa Xaa Xaa Xaa
                55
Xaa Xaa Xaa Xaa Xaa Xaa Cys
60                      65
Cys Xaa Pro Xaa Xaa Xaa Xaa Xaa
                70
Xaa Xaa Xaa Leu Xaa Xaa Xaa
75                      80
Xaa Xaa Xaa Xaa Val Xaa Leu Xaa
            85
Xaa Xaa Xaa Xaa Met Xaa Val Xaa
90                      95
Xaa Cys Gly Cys Xaa
            100
``` wherein each Xaa is independently selected from a group of one or more specified amino acids as defined by the following: "Res." means "residue" and Xaa at res.2=(Lys or Arg); Xaa at res.3=(Lys or Arg); Xaa at res.4=(His or Arg); Xaa at res.5=(Glu, Ser, His, Gly, Arg or Pro); Xaa at res.9=(Ser, Arg, Asp or Glu); Xaa at res.11=(Arg, Gln, Ser or Lys); Xaa at res.12=(Asp or Glu); Xaa at res.13=(Leu or Val); Xaa at res.16=(Gln, Leu, Asp, His or Asn); Xaa at res.17=(Asp, Arg, or Asn); Xaa at res.19=(Ile or Val); Xaa at res.20=(Ile or Val); Xaa at res.23=(Glu, Gln, Leu, Lys, Pro or Arg); Xaa at res.25=(Tyr or Phe); Xaa at res.26=(Ala, Ser, Asp, Met, His, Leu, or Gln); Xaa at res.28=(Tyr, Asn or Phe); Xaa at res.31=(Glu, His, Tyr, Asp or Gln); Xaa at res.33=Glu, Lys, Asp or Gln); Xaa at res.35=(Ala, Ser or Pro); Xaa at res.36=(Phe, Leu or Tyr); Xaa at res.38=(Leu or Val); Xaa at res.39=(Asn, Asp, Ala or Thr); Xaa at res.40=(Ser, Asp, Glu, Leu or Ala); Xaa at res.41=(Tyr, Cys, His, Ser or Ile); Xaa at res.42=(Met, Phe, Gly or Leu); Xaa at res. 43=(Asa or Ser) Xaa at res.44=(Ala, Ser or Gly); Xaa at res.45=(Thr, Leu or Ser); Xaa at res.49=(Ile or Val); Xaa at res.50=(Val or Leu); Xaa at res.51=(Gln or Arg); Xaa at res.52=(Thr, Ala or Ser); Xaa at res.54=(Val or Met); Xaa at res.55=(His or Asn); Xaa at res.56=(Phe, Leu, Asn, Ser, Ala or Val); Xaa at res.57=(Ile, Met, Asn, Ala or Val); Xaa at res.58=(Asn, Lys, Ala or Glu); Xaa at res.59=(Pro or Ser); Xaa at res.60=(Glu, Asp, or Gly); Xaa at res.61=(Thr, Ala, Val, Lys, Asp, Tyr, Ser or Ala); Xaa at res.62=(Val, Ala or Ile); Xaa at res.63=(Pro or Asp); Xaa at res.64=(Lys or Leu); Xaa at res.65=(Pro or Ala); Xaa at res.68=(Ala or Val); Xaa at res.70=(Thr or Ala); Xaa at res.71=(Gln, Lys, Arg or Glu); Xaa at res.72=(Leu, Met or Val); Xaa at res.73=(Asn, Ser or Asp); Xaa at res.74=(Ala, Pro or Ser); Xaa at res.75=(Ile, Thr or Val); Xaa at res.76=(Ser or Ala); Xaa at res.77=(Val or Met); Xaa at res.79=(Tyr or Phe); Xaa at res.80=(Phe, Tyr or Leu); Xaa at res.81=(Asp or Asn); Xaa at res.82=(Asp, Glu, Asn or Ser); Xaa at res.83=(Ser, Gln, Asn or Tyr); Xaa at res.84=(Ser, Asn, Asp or Glu); Xaa at res.85=(Asn, Thr or Lys); Xaa at res.87=(Ile or Val); Xaa at res.89=(Lys or Arg); Xaa at res.90=(Lys, Asn, Gln or His); Xaa at res.91=(Tyr, Ala or His); Xaa at res.92=(Arg, Gln or Glu); Xaa at res.93=(Asn, Glu or Asp); Xaa at res.95=(Val, Thr or Ala); Xaa at res.97=(Arg, Lys, Val, Asp or Glu); Xaa at res.98=(Ala, Gly or Glu); and Xaa at res.102=(His or Arg).

Particularly useful sequences include Vgl(fx), Vgr-1(fx), DPP(fx), OP1, OP2, CBMP-2A(fx), CBMP-2B(fx) and GDF-1(fx) (see Table II, infra, and (Seq. ID Nos. 5–14). In addition, biosynthetic constructs designed from the generic sequences, such as COP1, 3–5, 7, 16 (see Table III, infra, and Seq. ID Nos. 16–21) also are useful. Other useful sequences include the inhibins/activin proteins, and the BMP-3, BMP-5 and BMP-6 proteins. Still other useful sequences are those sharing at least 70% amino acid sequence homology, and preferably 80% homology with any of the sequences above. These are anticipated to include allelic and species variants and mutants, and biosynthetic muteins, as well as novel members of this morphogenic family of proteins.

Table II, set forth below compares the amino acid sequences of the active regions of native proteins that have been identified as morphogens, including human OP-1 (hOP-1, Seq. ID No. 5), mouse OP-1 (mOP-1, Seq. ID No. 6), human and mouse OP-2 (Seq. ID Nos. 7 and 8, respectively), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (Seq. ID No. 14.) In the table, three dots indicates that the amino acid in that position is the same as the amino acid in hOP-1. Three dashes indicates that no amino acid is present in that position, and are included for purposes of illustrating homologies. For example, amino acid residue 60 of CBMP-2A and CBMP-2B is "missing". Of course, both these amino acid sequences in this region comprise Asn-Ser (residues 58, 59), with CBMP-2A then comprising Lys and Ile, whereas CBMP-2B comprises Ser and Ile.

TABLE II

|  | Seq. ID No. |  |  |  |  |  |  |  |  |
|---|---|---|---|---|---|---|---|---|---|
| hOP-1 | 5 | Cys | Lys | Lys | His | Glu | Leu | Tyr | Val |
| mOP-1 | 6 | ... | ... | ... | ... | ... | ... | ... | ... |
| hOP-2 | 7 | ... | Arg | Arg | ... | ... | ... | ... | ... |
| mOP-2 | 8 | ... | Arg | Arg | ... | ... | ... | ... | ... |
| DPP | 11 | ... | Arg | Arg | ... | Ser | ... | ... | ... |
| Vgl | 12 | ... | ... | Arg | ... | His | ... | ... | ... |
| Vgr-1 | 13 | ... | ... | ... | ... | Gly | ... | ... | ... |
| CBMP-2A | 9 | ... | ... | Arg | ... | Pro | ... | ... | ... |
| CBMP-2B | 10 | ... | Arg | Arg | ... | Ser | ... | ... | ... |
| GDF-1 | 14 | ... | Arg | Ala | Arg | Arg | ... | ... | ... |
|  |  | 1 |  |  |  | 5 |  |  |  |
| hOP-1 |  | Ser | Phe | Arg | Asp | Leu | Gly | Trp | Gln | Asp |
| mOP-1 |  | ... | ... | ... | ... | ... | ... | ... | ... | ... |
| hOP-2 |  | ... | ... | Gln | ... | ... | ... | ... | Leu | ... |
| mOP-2 |  | Arg | ... | ... | ... | ... | ... | ... | Leu | ... |
| DPP |  | Asp | ... | Ser | ... | Val | ... | ... | Asp | ... |
| Vgl |  | Glu | ... | Lys | ... | Val | ... | ... | ... | Asn |
| Vgr-1 |  | ... | ... | Gln | ... | Val | ... | ... | ... | ... |
| CBMP-2A |  | Asp | ... | Ser | ... | Val | ... | ... | Asn | ... |
| CBMP-2B |  | Asp | ... | Ser | ... | Val | ... | ... | Asn | ... |
| GDF-1 |  | ... | ... | ... | Glu | Val | ... | ... | His | Arg |
|  |  |  | 10 |  |  |  |  | 15 |  |  |
| hOP-1 |  | Trp | Ile | Ile | Ala | Pro | Glu | Gly | Tyr | Ala |
| mOP-1 |  | ... | ... | ... | ... | ... | ... | ... | ... | ... |
| hOP-2 |  | ... | Val | ... | ... | ... | Gln | ... | ... | Ser |
| mOP-2 |  | ... | Val | ... | ... | ... | Gln | ... | ... | Ser |
| DPP |  | ... | Val | ... | ... | ... | Leu | ... | ... | Asp |
| Vgl |  | ... | Val | ... | ... | ... | Gln | ... | ... | Met |
| Vgr-1 |  | ... | ... | ... | ... | ... | Lys | ... | ... | ... |
| CBMP-2A |  | ... | ... | Val | ... | ... | Pro | ... | ... | His |
| CBMP-2B |  | ... | ... | Val | ... | ... | Pro | ... | ... | Gln |
| GDF-1 |  | ... | Val | ... | ... | ... | Arg | ... | Phe | Leu |
|  |  |  |  | 20 |  |  |  |  | 25 |  |
| hOP-1 |  | Ala | Tyr | Tyr | Cys | Glu | Gly | Glu | Cys | Ala |
| mOP-1 |  | ... | ... | ... | ... | ... | ... | ... | ... | ... |
| hOP-2 |  | ... | ... | ... | ... | ... | ... | ... | ... | Ser |
| mOP-2 |  | ... | ... | ... | ... | ... | ... | ... | ... | ... |

TABLE II-continued

| | | | | | | | | |
|---|---|---|---|---|---|---|---|---|
| DPP | ... | ... | ... | ... | His | ... | Lys | ... | Pro |
| Vgl | ... | Asn | ... | ... | Tyr | ... | ... | ... | Pro |
| Vgr-1 | ... | Asn | ... | ... | Asp | ... | ... | ... | Ser |
| CBMP-2A | ... | Phe | ... | ... | His | ... | Glu | ... | Pro |
| CBMP-2B | ... | Phe | ... | ... | His | ... | Asp | ... | Pro |
| GDF-1 | ... | Asn | ... | ... | Gln | ... | Gln | ... | ... |
| | | | | 30 | | | | 35 |

| | | | | | | | | |
|---|---|---|---|---|---|---|---|---|
| hOP-1 | Phe | Pro | Leu | Asn | Ser | Tyr | Met | Asn | Ala |
| mOP-1 | ... | ... | ... | ... | ... | ... | ... | ... | ... |
| hOP-2 | ... | ... | ... | Asp | ... | Cys | ... | ... | ... |
| mOP-2 | ... | ... | ... | Asp | ... | Cys | ... | ... | ... |
| DPP | ... | ... | ... | Ala | Asp | His | Phe | ... | Ser |
| Vgl | Tyr | ... | ... | Thr | Glu | Ile | Leu | ... | Gly |
| Vgr-1 | ... | ... | ... | ... | Ala | His | ... | ... | ... |
| CBMP-2A | ... | ... | ... | Ala | Asp | His | Leu | ... | Ser |
| CBMP-2B | ... | ... | ... | Ala | Asp | His | Leu | ... | Ser |
| GDF-1 | Leu | ... | Val | Ala | Leu | Ser | Gly | Ser** | ... |
| | | | | 40 | | | | |

| | | | | | | | | |
|---|---|---|---|---|---|---|---|---|
| hOP-1 | Thr | Asn | His | Ala | Ile | Val | Gln | Thr | Leu |
| mOP-1 | ... | ... | ... | ... | ... | ... | ... | ... | ... |
| hOP-2 | ... | ... | ... | ... | ... | Leu | ... | Ser | ... |
| mOP-2 | ... | ... | ... | ... | ... | Leu | ... | Ser | ... |
| DPP | ... | ... | ... | ... | Val | ... | ... | ... | ... |
| Vgl | Ser | ... | ... | ... | ... | ... | ... | ... | ... |
| Vgr-1 | ... | ... | ... | ... | ... | ... | ... | ... | ... |
| CBMP-2A | ... | ... | ... | ... | ... | ... | ... | ... | ... |
| CBMP-2B | ... | ... | ... | ... | ... | ... | ... | ... | ... |
| GDF-1 | Leu | ... | ... | ... | Val | Leu | Arg | Ala | ... |
| | 45 | | | | | 50 | | | |

| | | | | | | | | |
|---|---|---|---|---|---|---|---|---|
| hOP-1 | Val | His | Phe | Ile | Asn | Pro | Glu | Thr | Val |
| mOP-1 | ... | ... | ... | ... | ... | ... | Asp | ... | ... |
| hOP-2 | ... | His | Leu | Met | Lys | ... | Asn | Ala | ... |
| mOP-2 | ... | His | Leu | Met | Lys | ... | Asp | Val | ... |
| DPP | ... | Asn | Asn | Asn | ... | ... | Gly | Lys | ... |
| Vgl | ... | ... | Ser | ... | Glu | ... | ... | Asp | Ile |
| Vgr-1 | ... | ... | Val | Met | ... | ... | ... | Tyr | ... |
| CBMP-2A | ... | Asn | Ser | Val | ... | Ser | --- | Lys | Ile |
| CBMP-2B | ... | Asn | Ser | Val | ... | Ser | --- | Ser | Ile |
| GDF-1 | Met | ... | Ala | Ala | Ala | ... | Gly | Ala | Ala |
| | | 55 | | | | | 60 | | |

| | | | | | | | | |
|---|---|---|---|---|---|---|---|---|
| hOP-1 | Pro | Lys | Pro | Cys | Cys | Ala | Pro | Thr | Gln |
| mOP-1 | ... | ... | ... | ... | ... | ... | Asp | ... | ... |
| hOP-2 | ... | ... | Ala | ... | ... | ... | ... | ... | Lys |
| mOP-2 | ... | ... | Ala | ... | ... | ... | ... | ... | Lys |
| DPP | ... | ... | Ala | ... | ... | Val | ... | ... | ... |
| Vgl | ... | Leu | ... | ... | ... | Val | ... | ... | Lys |
| Vgr-1 | ... | ... | ... | ... | ... | ... | ... | ... | Lys |
| CBMP-2A | ... | ... | Ala | ... | ... | Val | ... | ... | Glu |
| CBMP-2B | ... | ... | Ala | ... | ... | Val | ... | ... | Glu |
| GDF-1 | Asp | Leu | ... | ... | ... | Val | ... | Ala | Arg |
| | | 65 | | | | | 70 | | |

| | | | | | | | | |
|---|---|---|---|---|---|---|---|---|
| hOP-1 | Leu | Asn | Ala | Ile | Ser | Val | Leu | Tyr | Phe |
| mOP-1 | ... | ... | ... | ... | ... | ... | ... | ... | ... |
| hOP-2 | ... | Ser | ... | Thr | ... | ... | ... | ... | Tyr |
| mOP-2 | ... | Ser | ... | Thr | ... | ... | ... | ... | Tyr |
| Vgl | Met | Ser | Pro | ... | ... | Met | ... | Phe | Tyr |
| Vgr-1 | ... | ... | ... | ... | ... | ... | ... | ... | ... |
| DPP | ... | Asp | Ser | Val | Ala | Met | ... | ... | Leu |
| CBMP-2A | ... | Ser | ... | ... | ... | Met | ... | ... | Leu |
| CBMP-2B | ... | Ser | ... | ... | ... | Met | ... | ... | Leu |
| GDF-1 | ... | Ser | Pro | ... | ... | ... | ... | Phe | ... |
| | | | 75 | | | | | 80 | |

| | | | | | | | | |
|---|---|---|---|---|---|---|---|---|
| hOP-1 | Asp | Asp | Ser | Ser | Asn | Val | Ile | Leu | Lys |
| mOP-1 | ... | ... | ... | ... | ... | ... | ... | ... | ... |
| hOP-2 | ... | Glu | ... | Asn | ... | ... | ... | ... | Arg |
| mOP-2 | ... | Ser | ... | Asn | ... | ... | ... | ... | Arg |
| DPP | Asn | ... | Gln | ... | Thr | ... | Val | ... | ... |
| Vgl | ... | ... | Asn | Asp | ... | ... | Val | ... | Arg |
| Vgr-1 | ... | ... | Asn | ... | ... | ... | ... | ... | ... |
| CBMP-2A | ... | Glu | Asn | Glu | Lys | ... | Val | ... | ... |
| CBMP-2B | ... | Glu | Tyr | Asp | Lys | ... | Val | ... | ... |
| GDF-1 | ... | Asn | ... | Asp | ... | ... | Va | ... | Arg |
| | | | | | 85 | | | | |

TABLE II-continued

|         |     |     |     |     |     |     |     |     |
|---------|-----|-----|-----|-----|-----|-----|-----|-----|
| hOP-1   | Lys | Tyr | Arg | Asn | Met | Val | Val | Arg |
| mOP-1   | ... | ... | ... | ... | ... | ... | ... | ... |
| hOP-2   | ... | Ala | ... | ... | ... | ... | ... | Lys |
| mOP-2   | ... | His | ... | ... | ... | ... | ... | Lys |
| DPP     | Asn | ... | Gln | Glu | ... | Thr | ... | Val |
| Vgl     | His | ... | Glu | ... | ... | Ala | ... | Asp |
| Vgr-1   | ... | ... | ... | ... | ... | ... | ... | ... |
| CBMP-2A | Asn | ... | Gln | Asp | ... | ... | ... | Glu |
| CBMP-2B | Asn | ... | Gln | Glu | ... | ... | ... | Glu |
| GDF-1   | Gln | ... | Glu | Asp | ... | ... | ... | Asp |
|         | 90  |     |     |     | 95  |     |     |     |
| hOP-1   | Ala | Cys | Gly | Cys | His |     |     |     |
| mOP-1   | ... | ... | ... | ... | ... |     |     |     |
| hOP-2   | ... | ... | ... | ... | ... |     |     |     |
| mOP-2   | ... | ... | ... | ... | ... |     |     |     |
| DPP     | Gly | ... | ... | ... | Arg |     |     |     |
| Vgl     | Glu | ... | ... | ... | Arg |     |     |     |
| Vgr-1   | ... | ... | ... | ... | ... |     |     |     |
| CBMP-2A | Gly | ... | ... | ... | Arg |     |     |     |
| CBMP-2B | Gly | ... | ... | ... | Arg |     |     |     |
| GDF-1   | Glu | ... | ... | ... | Arg |     |     |     |
|         |     |     | 100 |     |     |     |     |     |

**Between residues 43 and 44 of GDF-1 lies the amino acid sequence Gly-Gly-Pro-Pro.

Table III, set forth below, compares the amino acid sequence data for six related biosynthetic constructs designated COPs 1, 3, 4, 5, 7, and 16 (Seq. ID Nos. 16–21, respectively). As with Table II, the dots mean that in that position there is an identical amino acid to that of COP-1, and dashes mean that the COP-1 amino acid is missing at that position.

TABLE III

|        | Seq. ID No. |     |     |     |     |     |     |     |     |     |
|--------|-------------|-----|-----|-----|-----|-----|-----|-----|-----|-----|
| COP-1  | 16          | Leu | Tyr | Val | Asp | Phe | Gln | Arg | Asp | Val |
| COP-3  | 17          | ... | ... | ... | ... | ... | ... | ... | ... | ... |
| COP-4  | 18          | ... | ... | ... | ... | ... | Ser | --- | ... | ... |
| COP-5  | 19          | ... | ... | ... | ... | ... | Ser | --- | ... | ... |
| COP-7  | 20          | ... | ... | ... | ... | ... | Ser | --- | ... | ... |
| COP-16 | 21          | ... | ... | ... | ... | ... | Ser | --- | ... | ... |
|        |             | 1   |     |     |     | 5   |     |     |     |     |
| COP-1  | Gly | Trp | Asp | Asp | Trp | Ile | Ile | Ala |
| COP-3  | ... | ... | ... | ... | ... | ... | Val | ... |
| COP-4  | ... | ... | ... | ... | ... | ... | Val | ... |
| COP-5  | ... | ... | ... | ... | ... | ... | Val | ... |
| COP-7  | ... | ... | Asn | ... | ... | ... | Val | ... |
| COP-16 | ... | ... | Asn | ... | ... | ... | Val | ... |
|        | 10  |     |     |     | 15  |     |     |     |
| COP-1  | Pro | Val | Asp | Phe | Asp | Ala | Tyr | Tyr |
| COP-3  | ... | Pro | Gly | Tyr | Gln | ... | Phe | ... |
| COP-4  | ... | Pro | Gly | Tyr | Gln | ... | Phe | ... |
| COP-5  | ... | Pro | Gly | Tyr | Gln | ... | Phe | ... |
| COP-7  | ... | Pro | Gly | Tyr | His | ... | Phe | ... |
| COP-16 | ... | Pro | Gly | Tyr | Gln | ... | Phe | ... |
|        |     | 20  |     |     |     | 25  |     |     |
| COP-1  | Cys | Ser | Gly | Ala | Cys | Gln | Phe | Pro |
| COP-3  | ... | ... | ... | ... | ... | ... | ... | ... |
| COP-4  | ... | ... | ... | ... | ... | ... | ... | ... |
| COP-5  | ... | His | ... | Glu | ... | Pro | ... | ... |
| COP-7  | ... | His | ... | Glu | ... | Pro | ... | ... |
| COP-16 | ... | His | ... | Glu | ... | Pro | ... | ... |
| COP-1  | Ser | Ala | Asp | His | Phe | Asn | Ser | Thr |
| COP-3  | ... | ... | ... | ... | ... | ... | ... | ... |
| COP-4  | ... | ... | ... | ... | ... | ... | ... | ... |
| COP-5  | Leu | ... | ... | ... | ... | ... | ... | ... |

TABLE III-continued

| COP-7  | Leu | ... | ... | ... | Leu | ... | ... | ... |
|--------|-----|-----|-----|-----|-----|-----|-----|-----|
| COP-16 | Leu | ... | ... | ... | ... | ... | ... | ... |
|        | 35  |     |     |     | 40  |     |     |     |
| COP-1  | Asn | His | Ala | Val | Val | Gln | Thr | Leu | Val |
| COP-3  | ... | ... | ... | ... | ... | ... | ... | ... | ... |
| COP-4  | ... | ... | ... | ... | ... | ... | ... | ... | ... |
| COP-5  | ... | ... | ... | ... | ... | ... | ... | ... | ... |
| COP-7  | ... | ... | ... | ... | ... | ... | ... | ... | ... |
| COP-16 | ... | ... | ... | ... | ... | ... | ... | ... | ... |
|        |     |     |     |     | 45  |     |     |     | 50  |
| COP-1  | Asn | Asn | Met | Asn | Pro | Gly | Lys | Val |
| COP-3  | ... | ... | ... | ... | ... | ... | ... | ... |
| COP-4  | ... | ... | ... | ... | ... | ... | ... | ... |
| COP-5  | ... | Ser | Val | ... | Ser | Lys | Ile | --- |
| COP-7  | ... | Ser | Val | ... | Ser | Lys | Ile | --- |
| COP-16 | ... | Ser | Val | ... | Ser | Lys | Ile | --- |
|        |     |     |     |     | 55  |     |     |     |
| COP-1  | Pro | Lys | Pro | Cys | Cys | Val | Pro | Thr |
| COP-3  | ... | ... | ... | ... | ... | ... | ... | ... |
| COP-4  | ... | ... | ... | ... | ... | ... | ... | ... |
| COP-5  | ... | ... | Ala | ... | ... | ... | ... | ... |
| COP-7  | ... | ... | Ala | ... | ... | ... | ... | ... |
| COP-16 | ... | ... | Ala | ... | ... | ... | ... | ... |
|        |     | 60  |     |     |     | 65  |     |     |
| COP-1  | Glu | Leu | Ser | Ala | Ile | Ser | Met | Leu |
| COP-3  | ... | ... | ... | ... | ... | ... | ... | ... |
| COP-4  | ... | ... | ... | ... | ... | ... | ... | ... |
| COP-5  | ... | ... | ... | ... | ... | ... | ... | ... |
| COP-7  | ... | ... | ... | ... | ... | ... | ... | ... |
| COP-16 | ... | ... | ... | ... | ... | ... | ... | ... |
|        |     |     | 70  |     |     |     |     |     |
| COP-1  | Tyr | Leu | Asp | Glu | Asn | Ser | Thr | Val |
| COP-3  | ... | ... | ... | ... | ... | Glu | Lys | ... |
| COP-4  | ... | ... | ... | ... | ... | Glu | Lys | ... |
| COP-5  | ... | ... | ... | ... | ... | Glu | Lys | ... |
| COP-7  | ... | ... | ... | ... | ... | Glu | Lys | ... |
| COP-16 | ... | ... | ... | ... | ... | Glu | Lys | ... |
|        | 75  |     |     |     | 80  |     |     |     |
| COP-1  | Val | Leu | Lys | Asn | Tyr | Gln | Glu | Met |
| COP-3  | ... | ... | ... | ... | ... | ... | ... | ... |

TABLE III-continued

| COP-4 | ... | ... | ... | ... | ... | ... | ... | ... |
|---|---|---|---|---|---|---|---|---|
| COP-5 | ... | ... | ... | ... | ... | ... | ... | ... |
| COP-7 | ... | ... | ... | ... | ... | ... | ... | ... |
| COP-16 | ... | ... | ... | ... | ... | ... | ... | ... |
| | | 85 | | | | | 90 | |
| COP-1 | Thr | Val | Val | Gly | Cys | Gly | Cys | Arg |
| COP-3 | Val | ... | Glu | ... | ... | ... | ... | ... |
| COP-4 | Val | ... | Glu | ... | ... | ... | ... | ... |
| COP-5 | Val | ... | Glu | ... | ... | ... | ... | ... |
| COP-7 | Val | ... | Glu | ... | ... | ... | ... | ... |
| COP-16 | Val | ... | Glu | ... | ... | ... | ... | ... |
| | | | 95 | | | | | |

The foregoing and other objects, features, and advantages of the present invention will be made more apparent from the following detailed description of the invention.

DETAILED DESCRIPTION OF THE INVENTION

Figure 1:
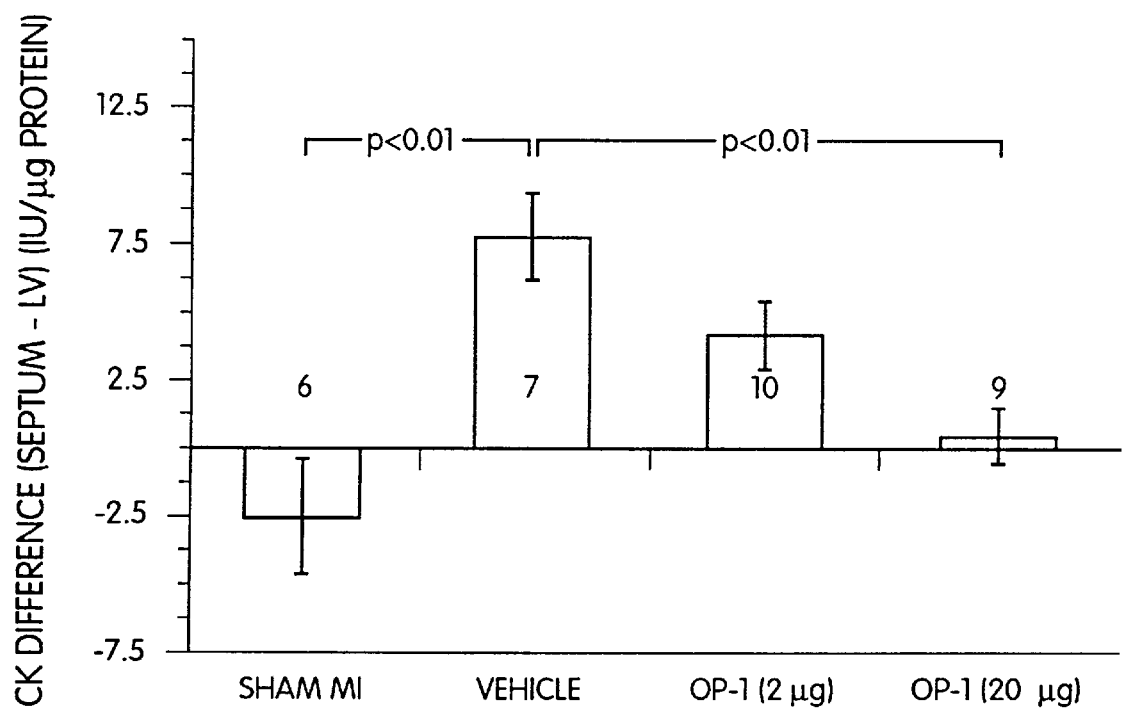
FIG. 1 shows the cardioprotective effects of morphogen (hOP1) in rat myocardial infarction plus reperfusion, as evidenced by the smaller loss of myocardial creatine kinase in hOP1-treated rats.

It now has been surprisingly discovered that the morphogens defined herein are effective agents in alleviating the tissue destructive effects associated with the body's inflammatory response to tissue injury. In particular, as disclosed herein, the morphogens are capable of alleviating the necrotic tissue effects associated with the ensuing inflammatory responses that occur following the tissue injury induced by cell exposure to toxic oxygen concentrations, such as ischemic-reperfusion tissue injury (oxygen deprivation), and hyperoxia injury (lethally high oxygen concentrations). Accordingly, the process of the present invention provides a method for alleviating ischemic-reperfusion injury or hyperoxia-induced injury comprising the step of administering to the afflicted individual a therapeutic amount of a morphogen prior to, during, or after damage to the affected tissue. Where the toxic oxygen concentrations may be deliberately induced, as by a surgical or clinical procedure, the morphogen preferably is administered prior to induction.

When tissue injury occurs, whether caused by bacteria, trauma, chemicals, heat, or any other phenomenon, the body's inflammatory response is stimulated. In response to signals released from the damaged cells (e.g., cytokines), extravascularization of immune effector cells is induced. Under ordinary circumstances these invading immune effector cells kill the infectious agent and/or infected or damaged cells (through the release of killing substances such as superoxide, performs, and other antimicrobial agents stored in granules), remove the dead tissues and organisms (through phagocytosis), release various biological response modifiers that promote rapid healing and covering of the wound (quite often resulting in the formation of scar tissue), and then, after the area is successfully healed, exit from the site of the initial insult. Once the site is perceived to be normal, the local release of inflammatory cytokines ceases and the display of adhesion molecules on the vessel endothelium returns to basal levels. In some cases, however, the zeal of these interacting signals and cellular systems, which are designed to capture and contain very rapidly multiplying infectious agents, act to the detriment of the body, killing additional, otherwise healthy, surrounding tissue. This additional unnecessary tissue death further complicates organ function and sometimes results in death of the patient.

The vascular endothelium constitutes the first barrier between circulating immune effector cells and extravascular tissues. Extravasation of these circulating cells requires that they bind to the vascular endothelial cells, cross the basement membrane, and enter insulted tissues. Without being limited to a particular theory, it is believed that the morphogens of this invention may modulate the inflammatory response by modulating the attachment of immune effector cells to the luminal side of the endothelium of blood vessels at or near sites of tissue damage and/or inflammatory lesions. Because the method reduces or prevents the attachment of immune effector cells at these sites, it also prevents the subsequent release of tissue destructive agents by these same immune effector cells at sites of tissue damage and/or inflammatory lesions. Because attachment of immune effector cells to the endothelium must precede their extravascularization, the method also prevents the initial or continued entry of these cells into extravascular sites of tissue destruction or ongoing inflammatory lesions. Therefore, the invention not only relates to a method to reduce or prevent the immune cell-mediated cellular destruction at extravascular sites of recent tissue destruction, but also relates to a method to prevent or reduce the continued entry of immune effector cells into extravascular sites of ongoing inflammatory cascades. As will be appreciated by those skilled in the art, the morphogens of this invention also may be contemplated in mechanisms for disrupting the functional interaction of immune effector cells with endothelium where the adhesion molecules are induced by means other than in response to tissue injury.

As defined herein, a protein is morphogenic if it is capable of inducing the developmental cascade of cellular and molecular events that culminate in the formation of new, organ-specific tissue and comprises at least the conserved C-terminal six cysteine skeleton or its functional equivalent (see supra). Details of how the morphogens useful in the method of this invention first were identified, as well as a description on how to make, use and test them for morphogenic activity are disclosed in copending U.S. Ser. No. 08/404,113, filed Mar. 14, 1995, pending, as a continuation of now-abandoned U.S. Ser. No. 08/091,395, filed Jul. 13, 1993 as a continuation of now-abandoned U.S. Ser. No. 07/752,764, filed Aug. 30, 1991 as a continuation-in-part of now-abandoned U.S. Ser. No. 07/667,274, filed Mar. 11, 1991, the disclosures of which are hereby incorporated by reference.

A candidate morphogen or morphogen composition can be evaluated for in vivo morphogenic utility generally according to the procedures set forth in U.S. Ser. No 08/404,113, pending. The proteins and compositions may be injected or surgically implanted in a mammal, following any of a number of procedures well known in the art. For example, surgical implant bioassays may be performed essentially following the procedure of Sampath et al. (1983) *PNAS* 80:6591–6595.

Histological sectioning and staining is preferred to determine the extent of morphogenesis in vivo, particularly in tissue repair procedures. Excised implants are fixed in Bouins Solution, embedded in paraffin, and cut into 6–8 µm sections. Staining with toluidine blue or hemotoxylin/eosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include:

(1) leukocytes on day one;
(2) mesenchymal cell migration and proliferation on days two and three;
(3) chondrocyte appearance on days five and six;
(4) cartilage matrix formation on day seven;
(5) cartilage calcification on day eight;
(6) vascular invasion, appearance of osteoblasts, and formation of new bone on days nine and ten;
(7) appearance of osteoblastic and bone remodeling and dissolution of the implanted matrix on days twelve to eighteen; and
(8) hematopoietic bone marrow differentiation in the ossicle on day twenty-one.

In addition to histological evaluation, biological markers may be used as a marker for tissue morphogenesis. Useful markers include tissue-specific enzymes whose activity may be assayed (e.g., spectrophotometrically) after homogenization of the implant. These assays may be useful for quantitation and for obtaining an estimate of tissue formation quickly after the implants are removed from the animal. For example, alkaline phosphatase activity may be used as a marker for osteogenesis.

Incorporation of systemically provided morphogens may be followed using tagged morphogens (e.g., radioactively labelled) and determining their localization in new tissue, and/or by monitoring their disappearance from the circulatory system using a standard pulse-chase labeling protocol. The morphogen also may be provided with a tissue-specific molecular tag, whose uptake may be monitored and correlated with the concentration of morphogen provided. As an example, ovary removal in female rats results in reduced bone alkaline phosphatase activity, rendering the rats predisposed to osteoporosis. If the female rats now are provided with a morphogen, e.g., OP-1, a reduction in the systemic concentration of calcium ($CA^{2+}$) is seen, which correlates with the presence of the provided morphogen and can be shown to correspond to increased alkaline phosphatase activity.

The morphogen to be assayed according to the above-described exemplary procedures can be purified from naturally-sourced material, or can be recombinantly produced from procaryotic or eucaryotic host cells, into which genetic material encoding a morphogen, e.g., genetic material bearing one of the nucleic acid sequences disclosed herein, has been introduced. Alternatively, the above-described exemplary procedures can be used to determine whether a novel protein suspected of being a morphogen indeed has morphogenic activity.

Particularly useful proteins include those which comprise the naturally derived sequences disclosed in Table II, including GDF-1(fx) and the biosynthetic constructs disclosed in Table III, as well as amino acid sequences sharing 70% or, preferably 80%, homology with any of these sequences.

Accordingly, morphogens useful in the method of this invention also can be described by any of the four generic sequences described supra (Generic Sequences 1, 2, 3 and 4). Generic sequences 1 and 2 also may include, at their N-terminus, the sequence (Seq. ID No.15)

$Cys_1$ Xaa Xaa Xaa $Xaa_5$.

In the method of this invention, the morphogen generally is administered to the individual parenterally, such as intravenously, in the form of an aqueous solution. The solution preferably is physiologically acceptable so that in addition to delivery of the desired morphogen to the patient the solution does not otherwise adversely affect the patient's electrolyte and volume balance. The aqueous medium for the morphogen thus usually comprises normal physiologic saline (9.85% NaCl, 0.15M), pH 7–7.4. The aqueous solution containing the morphogen can be made by dissolving the protein in 50% ethanol containing acetonitrile in 0.1% trifluoroacetic acid (TFA) or 0.1% HCl, or equivalent solvents. One volume of the resultant solution then is added to ten volumes of phosphate buffered saline (PBS), preferably containing 0.1–0.2% human serum albumin (HSA). The resultant solution preferably is vortexed extensively.

For purposes of the present invention, the above-described morphogens effective in alleviating ischemic-reperfusion injury are administered prior to or during the restoration of oxygen (e.g., restoration of blood flow, reperfusion.) Where treatment is to follow an existing injury, the morphogen preferably is administered as an intravenous infusion provided acutely after the hypoxic or ischemic condition occurs. For example, the morphogen can be administered by intravenous infusion immediately after a cerebral infarction, a myocardial infarction, asphyxia, or a cardiopulmonary arrest. Where ischemia or hypoxia is deliberately induced as part of, for example, a surgical procedure where circulation to an organ or organ system is deliberately and/or transiently interrupted, e.g., in carotid endarterectomy, coronary artery bypass, grafting, organ transplanting, fibrinolytic therapy, etc., the morphogen preferably is provided just prior to, or concomitant with, reduction of oxygen to the tissue. Preferably, the morphogen is administered prophylactically in a surgical setting. Optimally, the morphogen dosage given in all cases is between 2–20 µg of protein per kilogram weight of the patient.

Similarly, where hyperoxia already has occurred, the morphogen is administered upon diagnosis. Where hyperoxia may be induced as, for example, during treatment of prematurely newborn babies, or patients suffering from pulmonary diseases such as emphysema, the morphogen preferably is administered prior to administration of oxygen. The morphogen preferably is administered prophylactically at 2–20 µg protein per kilogram weight.

In administering morphogens in the method of the present invention, preferably a large volume loading dose is used at the start of the treatment. The treatment then is continued with a maintenance dose. Further administration then can be determined by monitoring at intervals the levels of the morphogen in the blood.

The suitability of the morphogens as therapeutic agents in the method of the present invention for alleviating injury associated with inflammatory response to tissue injury, particularly injury following exposure to toxic oxygen concentrations in a mammal is shown in the following, non-limiting examples.

EXAMPLE 1

Effect of Morphogen after the Onset of the Ischemic Process

The cardioprotective effect of morphogens following ischemic-reperfusion injury in a mammal can readily be assessed in a rat model. In this example, morphogen (OP1) is administered after the onset of the ischemic process in experimentally induced myocardial infarction in rats, essentially following the method of Lefer, et al. (1990) Science 249:61–64, the disclosure of which is hereby incorporated by reference. Briefly, loss of myocardial tissue function following ischemia and reperfusion is assayed by measuring loss of myocardial creatine kinease activity (CK) and loss of endothelium-dependent vasorelaxation function.

In a first group of ether-anesthetized rats, the left coronary artery was occluded just proximal to the first main branch with a silk ligature to induce a myocardial infarction (MI). The ligature was removed 10 minutes after occlusion to allow for coronary reperfusion. This first group is referred to herein as the "myocardial infarcted" (MI) group. A second group of rats underwent the same procedure except that the coronary artery was not occluded, and thus no myocardial infarction occurred. The second group of rats is referred to herein as the "sham myocardial infarcted group" (SHAM MI).

The first group of rats, the MI group of rats, further was divided into three sup-groups. 2 μg of morphogen (OP1) were injected intravenously into the first sub-group of MI rats 10 minutes after ligature, immediately before reperfusion later; into the second sub-group of MI rats 20 μg of OP1 were injected intravenously 10 minutes after ligature, immediately before reperfusion; and into the third sub-group of MI rats was injected the OP1 vehicle, acetate buffer alone, without any OP1.

Twenty-four hours later, the hearts were removed from all of the rats and the levels of creatine kinase (CK) from the left ventricle (the infarcted region) and from the interventricular septum (the control nonischemic region) were determined. By comparing the difference in CK activities in both regions, the amount of CK activity lost from the infarcted region was used as an index of cardiac cellular injury to the infarcted region.

The data shown in FIG. 1 indicate that OP1 reduces CK loss in myocardial tissue resulting from a myocardial infarction.

The loss of CK activity by the subgroup of MI rats which received 2 μg of OP1 was about 30% less than the control MI rats which received injections of vehicle alone, when the levels from both subgroups are measured against, and compared to, the levels obtained for the SHAM MI control.

Furthermore, the loss of CK activity by the subgroup of MI rats which received 20 μg of OP1 was about 75% less than the control MI rats which received injections of vehicle alone, when the levels from both subgroups are measured against, and compared to, the levels contained within the SHAM MI control.

These data indicate that OP1 offers significant cardiac protection even when administered after ischemia and before reperfusion. Similar experiments performed with TGF-β indicate that it also has some cardio-protective effects, although not as significant as those achieved with morphogen protein (see Lefer, et al., (1990) Science 249:61–64).

A variation of this example also may be performed providing morphogen to the animal prior to induction of ischemia. The experiments may be performed both in normal and immune-compromised rats to assess the cardioprotective effects of morphogen administered prior to ischemia.

EXAMPLE 2

Vasodilation of Myocardial Infarcted Cardiac Tissue Treated with Morphogen

Certain vasodilators like acetylcholine (ACh) and adenosine diphosphate (ADP, an immune mediator) exert their vasodilation activity only in the presence of intact endothelium, which is stimulated to release a substance termed endothelium-derived relaxing factor (EDRF). If the endothelium is injured so that EDRF is not released, no vasodilation occurs in response to these endothelium-dependent agents. In contrast, several other vasodilators including nitroglycerine (NTG) and nitroprusside, are endothelium-independent dilators, as they dilate blood vessels directly.

The present example demonstrates the ability of OP1 to prevent the loss of cardioendothelium-dependent relaxation (EDR) activity in the coronary microvasculature following reperfusion of ischemic myocardium, and the ability to reduce myocardial injury 24 hours after morphogen treatment. Briefly, 2 or 24 hours after morphogen treatment ischemia-reperfusion injury is induced, and rat hearts are vasodilated with either ACh or NTG In the absence of morphogen (OP1) treatment injured tissue should have reduced ACh-induced vasodilation, but not NTG-induced vasodilation.

Accordingly, 48 adult male Sprague-Dawley rats (250–330 g) were divided into eight groups of 6 rats. The rats were anesthetized with pentobarbital sodium (35 mg/kg, intraperitoneal); their hearts were isolated and perfused by the Langendorff method at a constant flow (15 ml/min) with oxygenated Krebs-Henseleit solution (Aoki et al. (1988) J. Pharmacol. 95:35). One set of twelve rats were intravenously injected with OP1 24 hours prior to isolation of the heart; another set of rats were intravenously injected with 20 μg of OP1 2 hours prior to isolation of the heart. The final group of rats was injected only with the 20 mM sodium acetate buffer (vehicle only).

Each group of rats then were divided into two subgroups of six rats each. Twenty minutes before reperfusion, coronary vasodilator response was measured by inducing constriction with 0.05 μmol U-44619 (9,11-methanoepoxyprostaglandin $H_2$) followed by a vasodilating agent 3 minutes later: subgroup one—15 nmol ACh; subgroup 2–15 nmol NTG.

Twelve rats were subjected to sham myocardial infarcts (SHAM MI) as described in Example 1. The remaining rat hearts were subjected to ischemia by reducing coronary infusion to 15% of control flow for 30 minutes, then reestablishing normal flow, i.e., reperfusion, for an additional 20 minutes.

Figure 2:
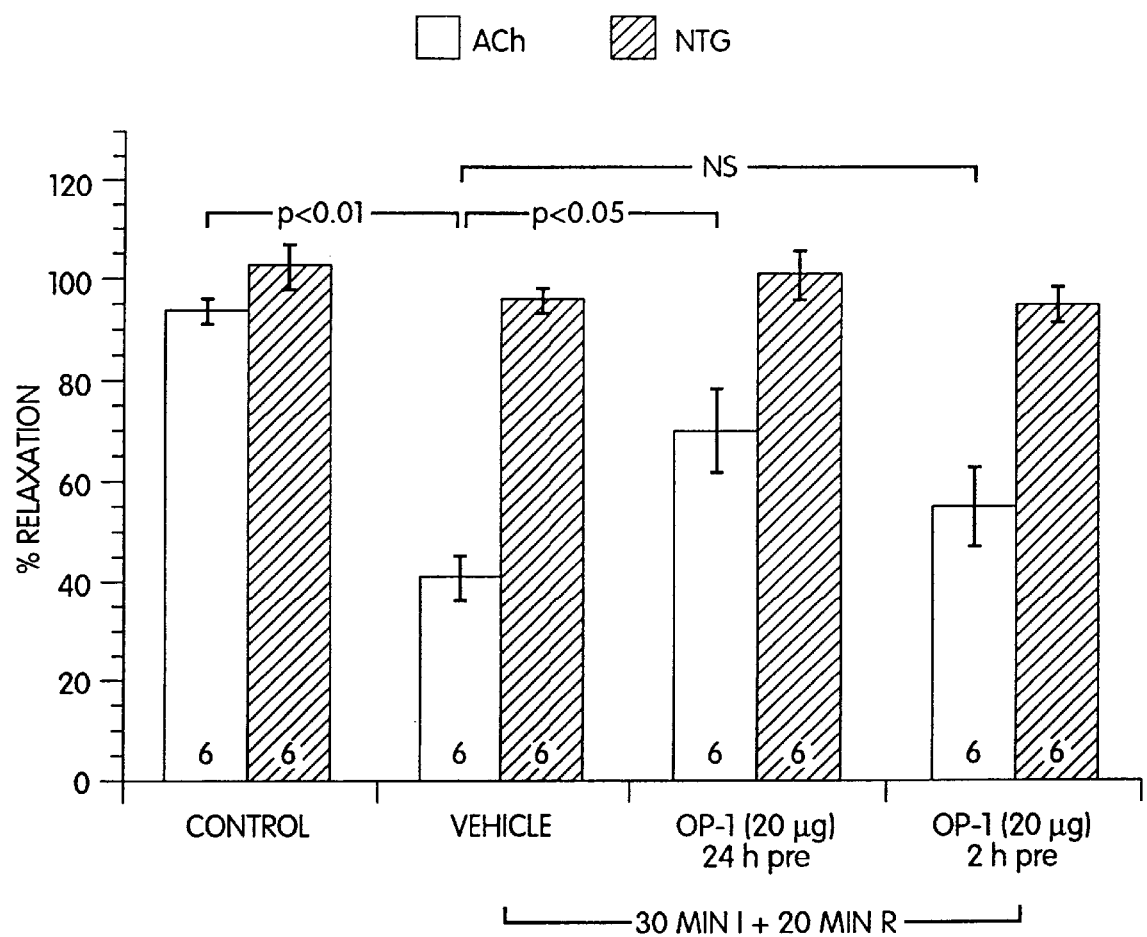
FIG. 2 shows the effects of 20 μg of morphogen (hOP1) given 24 hours prior to isolation of rat heart on endothelial-dependent vasorelaxation to acetycholine following induced ischemia-reperfusion injury.

The results of these experiments are shown in FIG. 2. The hearts which received OP1 24 hours prior to ischemia showed an approximately 70% response to ACh while the hearts which received OP1 2 hours prior to ischemia showed a 55% response to ACh. The group which only received the acetate buffer vehicle showed a 40% response to ACh. Finally, the control group which was not subjected to ischemia showed an ACh response of approximately 95%. This shows that endothelium-dependent vasodilators exert a reduced vasodilator response during myocardial ischemia and reperfusion in the rat heart. Moreover, OP1 significantly preserved endothelium-dependent dilation when provided 2 to 24 hours prior to induction of myocardial ischemia. No defect in vasodilation occurred in response to the direct vasodilator (NTG); NTG-induced vasodilation activities were 95% of initial in hearts subject to ischemia and 100% of initial nonischemic hearts.

EXAMPLE 3

Effect of Morphogen on Neutrophil Adherence

The role of neutrophil adherence in endothelium dysfunction and the cardioprotective effects of morphogens in modulating this activity can be assessed using a standard polymorphonuclear neutrophil (PMN) adherence assay. Briefly, segments of superior mesenteric artery were isolated from rats which had either been treated with morphogen (OP1, 20 μg) or 0.9% NaCl, 24 h prior to isolation of the arteries. The segments were cleaned, cut into transverse rings of 1–2 mm in length, and these were subsequently cut open and incubated in K-H solution at 37° C., pH 7.4. Neutrophils were prepared and fluorescently labelled using standard procedures (e.g., leukocytes were isolated from rats essentially following the procedure of Pertroft et. al. (1968) *Exp Cell Res* 50: 355–368, washed in phosphate buffered saline (PBS), purified by gradient centrifugation; and labelled by the method of Yuan et. al. (1990) *Microvasc Res* 40: 218–229.

Labelled neutrophils then were added to open ring baths and activated with 100 nM leukotriene $B_4$ ($LTB_4$). Rings were incubated for 20 minutes and the number of neutrophils adhering to the endothelial surface then determined visually by fluorescent microscopy.

Figure 3:
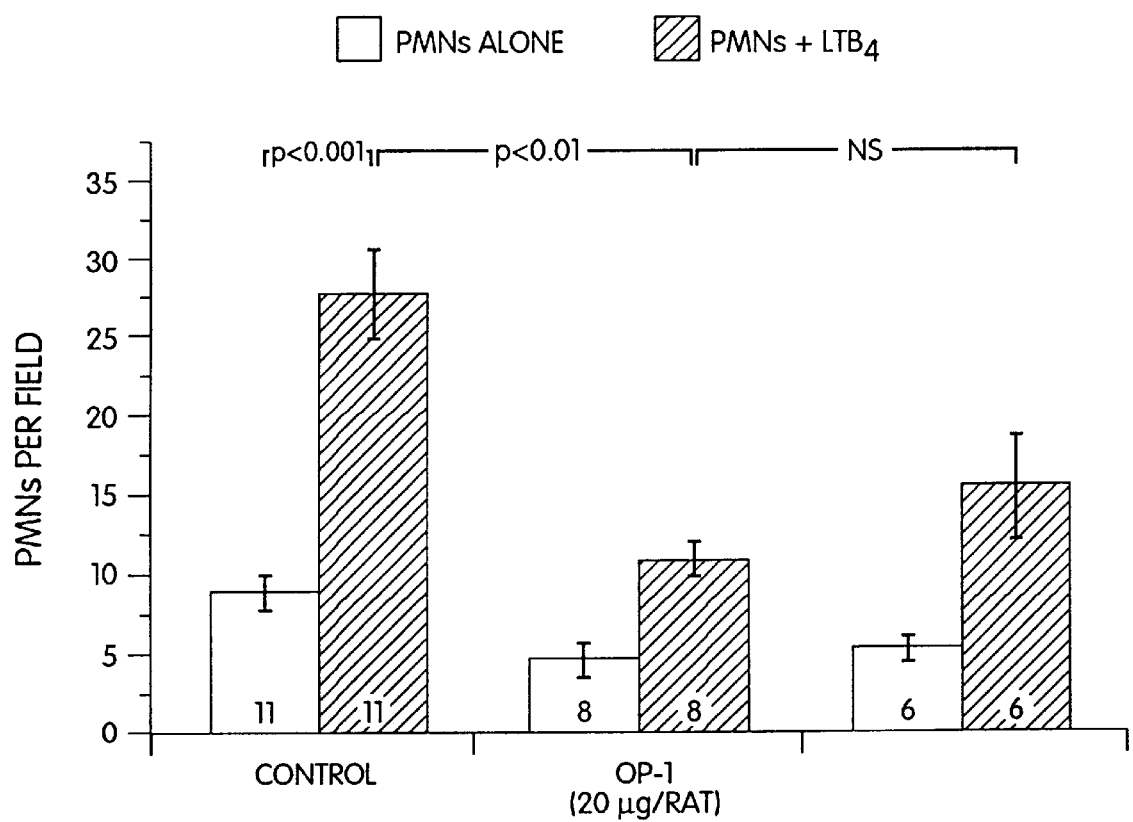
FIG. 3 shows the effect of morphogen (hOP1) on neutrophil adherence to $LTB_4$-stimulated mesenteric artery endothelium in neutrophil-activated rats.

As shown in FIG. 3, unstimulated PMNs (i.e., PMNs alone) added to the baths did not significantly adhere to the vascular endothelium. In rings taken from rats injected with 0.9% NaCl, activation of neutrophils with $LTB_4$ (100 nM) greatly increased the number of PMNs adherent to the endothelium ($P<0.001$). OP1 (20 μg administered 24 h prior) significantly inhibited adherence of PMNs activated by $LTB_4$ ($P<0.01$ from control).

ADDITIONAL EXAMPLES

Other tissues seriously affected by ischemic-reperfusion injury include neural tissue, renal tissue and lung tissue. The effect of morphogens on alleviating the ischemic-reperfusion injury in these tissues may be assessed using methodologies and models known to those skilled in the art, and disclosed below. Similarly, a methodology also is provided for assessing the tissue-protective effects of a morphogen on hyperoxia damaged lung tissue.

For example, the rabbit embolic stroke model provides a useful method for assessing the effect of morphogens on tissue injury following cerebral ischemia-reperfusion. The protocol disclosed below is essentially that of Phillips et al. (1989) *Annals of Neurology* 25:281–285, the disclosure of which is herein incorporated by reference. Briefly, white New England rabbits (2–3 kg) are anesthesized and placed on a respirator. The intracranial circulation then is selectively catheterized by the Seldinger technique. Baseline cerebral angiography then is performed, employing a digital substration unit. The distal internal carotid artery or its branches then is selectively embolized with 0.035 ml of 18-hour-aged autologous thrombus. Arterial occlusion is documented by repeat angiography immediately after embolization. After a time sufficient to induce cerebral infarcts (15 minutes or 90 minutes), reperfusion is induced by administering a bolus of a reperfusion agent such as the TPA analogue Fb-FB-CF (e.g., 0.8 mg/kg over 2 minutes).

The effect of morphogen on cerebral infarcts can be assessed by administering varying concentrations of morphogens, e.g., OP1, at different times following embolization and/or reperfusion. The rabbits are sacrificed 3–14 days post embolization and their brains prepared for neuropathological examination by fixing by immersion in 10% neutral buffered formation for at least 2 weeks. The brains then are sectioned in a coronal plane at 2–3 mm intervals, numbered and submitted for standard histological processing in paraffin, and the degree of neural tissue necrosis determined visually.

The renal-protective effects of morphogens on renal ischemia-reperfusion injury readily can be assessed using the mouse model disclosed by Oueliette, et al. (1990), *J. Clin. Invest.* 85:766–771, the disclosure of which is hereby incorporated by reference. Briefly, renal ischemia is induced surgically in 35–45 days old out-bred Swiss male mice by performing a standard right nephrectomy, and occluding the artery to the left kidney with a microaneurism clamp for 10–30 minutes. Morphogen then may be provided parenterally, post-reperfusion as described for Example 1. The effects of morphogen then may be assessed by biological evaluation.

The tissue protective effects of morphogen on tissue exposed to lethally high oxygen concentrations may be assessed by the following procedure. Adult rats (275–300 gms) first are provided with morphogen (e.g., hOP1) or vehicle only, and then are exposed to 96–98% oxygen essentially as described by Rinaldo et al (1983) *Am. Rev. Respir. Dis.* 130:1065, to induce hyperoxia. Animals are housed in plastic cages (38 cm×48 xm×21 cm). A cage containing 4–5 animals is placed in a 75 liter water-sealed plexiglass chamber. An atmosphere of 96–98% oxygen then is maintained by delivery of $O_2$ gas (liquid $O_2$). Gas flow through the chamber is adjusted to maintain at least 10 air changes/hr., temperature at 22±1° C., minimal levels of condensation within the cage, and carbon dioxide concentration of <0.5% as measured with a mass spetrophotometric medical gas analyzer.

At the end of 72 hours all survivors are observed at room air for 1.5 hours to assess degree of respiratory distress and cyanosis. The number of survivors at the end of the challenge is recorded and the treated groups compared with the untreated control group by chi-square test of proportions. Four surviving animals for each group are randomly chosen for histological processing of lung tissue.

Lung tissue for histological processing is fixed by infusion of 10% buffered formalin through a tracheal cannula at a constant pressure of 20 cm $H_2O$. After fixation for 24–48 hours, sections from each lobe are cut and subsequently stained with hematoxylin and eosin. Coded slides then are examined, preferably in a double-blind fashion for evidence of pathological changes such as edema, interstitial cellularity, and inflammatory response.

The present invention has been described in detail with particular reference to preferred embodiments thereof, but it will be understood that variations and modifications can be effected within the spirit and scope of the invention.

What is claimed is:

1. A method for treating immune cell mediated inflammatory response to ischemia-reperfusion or hyperoxia injury, the method comprising:
    administering a morphogen other than TGF-$\beta_2$ to tissue affected by an immune cell mediated inflammatory response, said morphogen comprising a dimeric protein having an amino acid sequence selected from the group consisting of
    (i) a sequence having at least 70% amino acid sequence homology with the C-terminal seven-cysteine skeleton of human OP-1, amino acids 38–139 of Seq. ID No.5; and
    (ii) an approximately 102 amino acid skeleton wherein cysteines occupy relative amino acid positions 1, 30, 34, 66, 67, 99, and 101, and wherein at least 70% of amino acids within said skeleton are identical to, or are conservative substitutions for, amino acids 38–139 of Seq. ID No.5, and
    wherein said morphogen induces endochondral bone formation in an in vivo assay.

2. The method of claim 1 wherein said administering morphogen is conducted after onset of ischemia and before reperfusion.

3. The method of claim 1 wherein said administering morphogen is conducted before onset of ischemia.

4. A method for reducing tissue damage associated with ischemia-reperfusion injury in a patient, the method comprising:
    administering a morphogen other than TGF-$\beta_2$ to the patient said morphogen comprising a dimeric protein having an amino acid sequence selected from the group consisting of
    (i) a sequence having at least 70% amino acid sequence homology with the C-terminal seven-cysteine skeleton of human OP-1, amino acids 38–139 of Seq. ID No. 5; and
    (ii) an approximately 102 amino acid skeleton wherein cysteines occupy relative amino acid positions 1, 30, 34, 66, 67, 99, and 101, and wherein at least 70% of amino acids within said sequence are identical to, or are conservative substitutions for, amino acids 38–139 of Seq. ID No.5, and
    wherein said morphogen induces endochondral bone formation in an in vivo assay.

5. A method for reducing tissue damage associated with hyperoxia injury in a patient, the method comprising:
    administering a morphogen other than TGF-$\beta_2$ to the patient, said morphogen comprising a dimeric protein having an amino acid sequence selected from the group consisting of
    (i) a sequence having at least 70% amino acid sequence homology with the C-terminal seven-cysteine skeleton of human OP-1, amino acids 38–139 of Seq. ID No. 5; and
    (ii) an approximately 102 amino acid skeleton wherein cysteines occupy relative amino acid positions 1, 30, 34, 66, 67, 99, and 101, and wherein at least 70% of amino acids within said sequence are identical to, or are conservative substitutions for, amino acids 38–139 of Seq. ID No. 5, and
    wherein said morphogen induces endochondral bone formation in an in vivo assay.

6. The method of claim 1, 4 or 5 wherein said tissue is selected from the group consisting of lung tissue, neural tissue, cardiac tissue, and renal tissue.

7. The method of claim 2 or 4 wherein said ischemic-reperfusion injury is associated with a condition selected from the group consisting of cardiac arrest, pulmonary occlusion, arterial occlusion, coronary occlusion, and occlusive stroke.

8. The method of claim 2 or 4 wherein said ischemic-reperfusion injury is associated with a myocardial infarction and the amino acid sequence of said morphogen comprises the C-terminal seven-cysteine skeleton of human OP-1, amino acids 38–139 of Seq. ID No. 5.

9. The method of claim 2 or 4 wherein said ischemic-reperfusion injury is associated with renal arterial occlusion and the amino acid sequence of said morphogen comprises the C-terminal seven-cysteine skeleton of human OP-1, amino acids 38–139 of Seq. ID No. 5.

10. The method of claim 2 or 4 wherein said ischemic-reperfusion injury is associated with cerebral embolization and the amino acid sequence of said morphogen comprises the C-terminal seven-cysteine skeleton of human OP-1, amino acids 38–139 of Seq. ID No.5.

11. The method of claim 2 or 4 wherein said administering morphogen is intravascular.

12. A method for reducing tissue damage associated with an interruption or reduction of blood flow to an organ or tissue in a patient caused by a clinical procedure other than an organ transplant procedure, the method comprising:

administering a morphogen other than TGF-$\beta_2$ to the patient prior to the interruption or reduction of blood flow, wherein said morphogen comprises a dimeric protein having an amino acid sequence selected from the group consisting of (i) a sequence having at least 70% amino acid sequence homology with the C-terminal seven-cysteine skeleton of human OP-1, amino acids 38–139 of Seq. ID No. 5; and (ii) an approximately 102 amino acid skeleton wherein cysteines occupy relative amino acid positions 1, 30, 34, 66, 67, 99, and 101, and wherein at least 70% of amino acids within said skeleton are identical to, or are conservative substitutions for, amino acids 38–139 of Seq. ID No. 5, and wherein said morphogen induces endochondral bone formation in an in vivo assay.

13. The method of claim 12 wherein said clinical procedure is selected from the group consisting of a carotid enterectomy, a coronary artery bypass, and a fibrinolytic therapy.

14. The method of claim 12 wherein said administering morphogen is intravascular.

15. The method of claim 1, 4, 5, or 12 wherein said administering morphogen is prophylactic.

16. The method of claim 1, 4, 5, or 12 wherein the amino acid sequence is selected from the group consisting of (i) a sequence having at least 80% amino acid sequence homology with said C-terminal seven-cysteine skeleton of human OP-1, and (ii) an approximately 102 amino acid skeleton wherein at least 80% of amino acids within said skeleton are identical to, or are conservative substitutions for, amino acids 38–139 of Seq. ID No. 5.

17. The method of claim 16 wherein said morphogen comprises an amino acid sequence selected from amino acids 38–139 of Seq. ID Nos. 5, 6, 7, or 8.

18. The method of claim 1, 4, 5, or 12 wherein said morphogen comprises an amino acid sequence selected from the group consisting of (a) Seq. ID No. 9, CBMP2A(fx);

(b) Seq. ID No. 10, CBMP2B(fx);

(c) Seq. ID No. 11, DPP(fx);

(d) Seq. ID No. 12, Vgl(fx);

(e) Seq. ID No. 13, Vgr-1(fx);

(f) Seq. ID No. 14, GDF-1(fx), and a naturally occurring or biosynthetic conservative substitution variant of any thereof, wherein said morphogen induces endochondral bone formation in an in vivo assay.

19. The method of claim 1, 4, 5, or 12 wherein said approximately 102 amino acid sequence has at least 101 amino acids.

20. The method of claim 1, 4, 5, or 12 wherein said approximately 102 amino acid sequence has at most 106 amino acids.

21. The method of claim 5 wherein said tissue damage is associated with oxygen treatment for pulmonary disease or premature birth.

22. The method of claim 21 wherein said tissue damage is associated with oxygen treatment for emphysema.

23. The method of claim 4 wherein said tissue damage is associated with atherosclerosis.

24. A method for treating immune cell mediated inflammatory response to ischemia-reperfusion or hyperoxia injury in a patient, the method comprising:

administering a morphogen other than TGF-$\beta_2$ to the patient, said morphogen comprising a dimeric protein having an amino acid sequence comprising the C-terminal seven-cysteine skeleton sequence of human OP-1, amino acids 38–139 of Seq. ID No. 5, or a variant of said skeleton sequence that is within the definition of Generic Sequence 4, Seq. ID No. 4, and wherein said morphogen induces endochondral bone formation in an in vivo assay.

* * * * *